(12) United States Patent
Suga et al.

(10) Patent No.: US 9,783,800 B2
(45) Date of Patent: Oct. 10, 2017

(54) METHOD FOR PRODUCING PEPTIDES HAVING AZOLE-DERIVED SKELETON

(71) Applicant: The University of Tokyo, Tokyo (JP)

(72) Inventors: Hiroaki Suga, Tokyo (JP); Yuki Goto, Tokyo (JP); Yasuharu Kato, Tokyo (JP)

(73) Assignee: The University of Tokyo, Tokyo (JP)

( * ) Notice: Subject to any disclaimer, the term of this patent is extended or adjusted under 35 U.S.C. 154(b) by 0 days.

(21) Appl. No.: 15/115,978

(22) PCT Filed: Feb. 3, 2015

(86) PCT No.: PCT/JP2015/052961
§ 371 (c)(1),
(2) Date: Nov. 15, 2016

(87) PCT Pub. No.: WO2015/115661
PCT Pub. Date: Aug. 6, 2015

(65) Prior Publication Data
US 2017/0159046 A1    Jun. 8, 2017

(30) Foreign Application Priority Data

Feb. 3, 2014  (JP) .................................. 2014-018847

(51) Int. Cl.
*C12N 15/10* (2006.01)
(52) U.S. Cl.
CPC ..... *C12N 15/1068* (2013.01); *C12N 15/1062* (2013.01)
(58) Field of Classification Search
None
See application file for complete search history.

(56) References Cited

U.S. PATENT DOCUMENTS

| 6,121,455 A | 9/2000 | Pitterna et al. |
| 2006/0161007 A1 | 7/2006 | Martin et al. |

(Continued)

FOREIGN PATENT DOCUMENTS

| JP | 2001-506254 A | 5/2001 |
| JP | 2002-540106 A | 11/2002 |

(Continued)

OTHER PUBLICATIONS

Creeke, et al., "Synthesis and elaboration of heterocycles via iodocyclisation of unsaturated thioureas", Jun. 29, 1989, pp. 4435-4438, vol. 30, No. 33, Publisher: Tetrahedron Letters.

(Continued)

*Primary Examiner* — Christopher M Gross

(74) *Attorney, Agent, or Firm* — Suzannah K. Sundby, Esq.; Canady + Lortz LLP

(57) ABSTRACT

Object of the present invention is to develop an artificial synthesis system of various peptides having an azole derivative structure and develop a library of such peptides. The present invention provides a method of producing a peptide having, in the backbone thereof, an azole derivative structure comprising the step of: synthesizing a substrate peptide of an azoline structure introducing enzyme having, in the modified region thereof, at least any one of the following amino acids,

[Chemical formula 1]

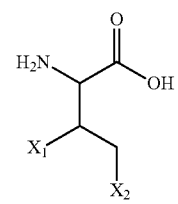

[Chemical formula 2]

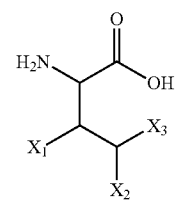

[Chemical formula 3]

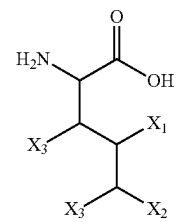

[Chemical formula 4]

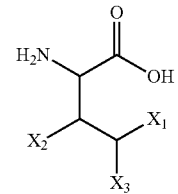

[in any of the compounds,
$X_1$ represents a group selected from the group consisting of SH, OH, $NH_2$, $SR^1$, $OR^1$, $NHR^1$, and $N_3$ ($R^1$ represents a protecting group),
$X_2$ represents an easily eliminable group; and
$X_3$ represents hydrogen or a substituted or unsubstituted alkyl or aryl group having from 1 to 10 carbon atoms];
reacting the substrate peptide with an azoline structure introducing enzyme to obtain a peptide having an azoline derivative structure; and (Continued)

converting the azoline derivative structure of the resulting peptide into an azole derivative structure by inducing an $HX_2$ elimination reaction of $X_2$ group.

20 Claims, 10 Drawing Sheets

(56) References Cited

U.S. PATENT DOCUMENTS

2009/0326020 A1    12/2009  Miller et al.
2014/0113830 A1    4/2014   Suga et al.

FOREIGN PATENT DOCUMENTS

JP    2011-524422 A    9/2011
WO    2009098453 A1    8/2009
WO    2012121392 A1    9/2012

OTHER PUBLICATIONS

International Search Report received in PCT/JP2015/052961, dated Apr. 28, 2015.
Stankova, et al., "Synthesis of thiazole, imidazole and oxazole containing amino acids for peptide backbone modification", Apr. 20, 1999, pp. 392-398, vol. 5, No. 9, Publisher: J. Peptide Science.
Written Opinion received in PCT/JP2015/052961, dated Apr. 28, 2015.

FIG. 7  MNKKNILPQQGQPVIRLTAGQLSSQLAELSEEALGDAGLEASVZAYDGVEPS

FIG. 8
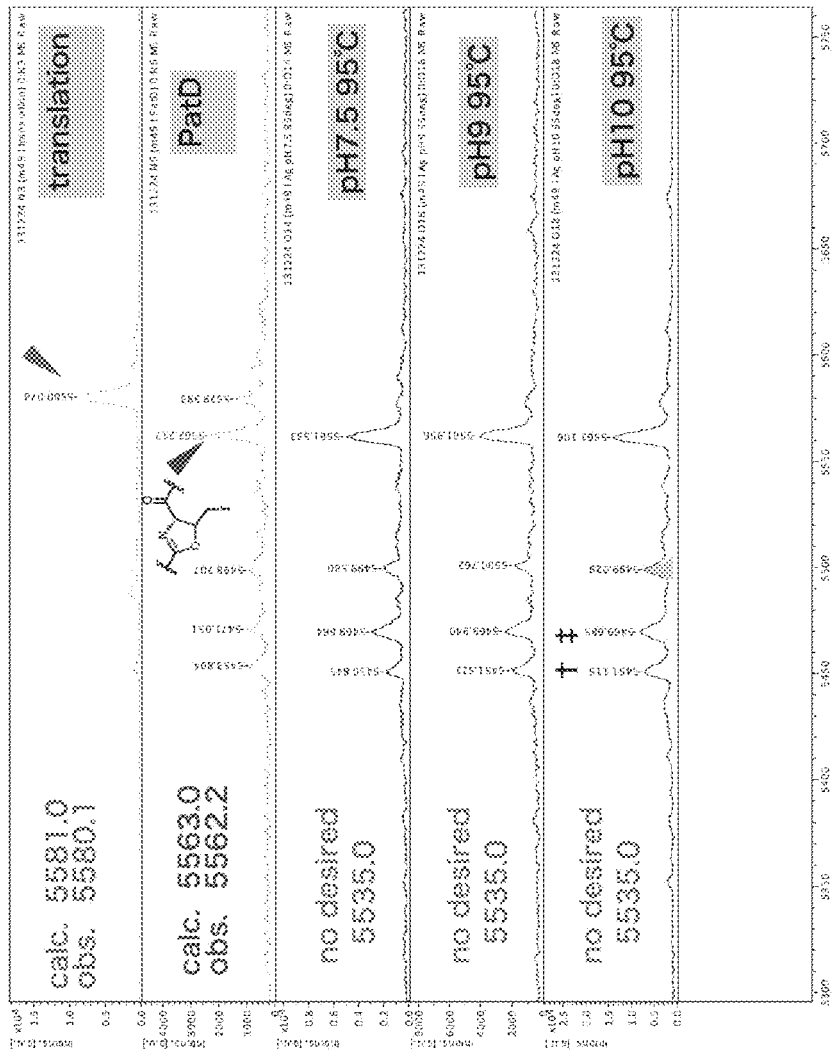

METHOD FOR PRODUCING PEPTIDES HAVING AZOLE-DERIVED SKELETON

TECHNICAL FIELD

The present invention relates to a method of producing peptides having an azole derivative structure, and the like.

BACKGROUND ART

Peptides have recently attracted attention as a drug candidate or research tool. There have been various attempts to develop a peptide library and screen peptides having affinity or physiological activity for a target substance.

Patellamide produced by Prochloron didemni, that is, endozoic algae of sea squirt is a low molecular cyclic peptide which is presumed to have various physiological activities. It is biosynthesized via a unique pathway with products of a pat gene cluster consisting of patA to patG. The pat gene cluster and biosynthesis pathway of it are schematically shown in FIG. 10.

In this biosynthesis, PatE peptide which is a patE gene product becomes a precursor. Since the patE gene has a hypervariable region (cassette region), the product of it constructs a natural combinatorial library.

The PatE peptide has, on both sides of the cassette region thereof, a recognition sequence by a post-translational modifying enzyme. Enzymes which serve as the post-translational modifying enzyme are PatA, PatD, and PatG. PatD introduces an azoline skeleton into Cys, Ser, and Thr in the cassette of PatE and converts Cys into a thiazoline structure and Ser and Thr into an oxazoline structure.

PatA cleaves the N-terminal recognition sequence of the cassette region of the PatE.

PatG is composed of two domains. An N-terminal oxidase domain converts a thiazoline structure introduced by PatD into a thiazole structure. A C-terminal peptidase domain macrocyclizes, while cleaving a C-terminal recognition sequence of the cassette region of PatE.

The present inventors have already found that the cassette region of PatE is modified by PatD even when the sequence of it is changed to a variety of sequences different from a natural one and have confirmed that library of azoline-structure-containing peptides much more rich in variety than that of natural PatE products can be produced using PatD (Patent Document 1).

On the other hand, peptides having an azole structure are expected to have properties such as higher peptidase resistance than those having an amide bond, excellent binding ability to a target due to a fixed structure, high affinity for metals or nucleic acids because they are converted into aromatic compounds having a π electronic system, and high membrane permeability due to loss of a hydrogen atom of an amide bond serving as a hydrogen bond donor. As a natural physiologically active peptide having azole as a backbone structure, known are patellamideD having inhibitory activity against multi-drug resistance of a leukemia cell strain and Telomestatin having telomerase inhibitory activity.

If a diverse library of azole-structure-containing peptides can be obtained, therefore, it is possible to enhance the possibility of selecting a peptide having binding ability or physiological activity for various target substances.

CITATION LIST

Patent Document

Patent Document 1: WO2012/121392

SUMMARY

Technical Problem

An object of the present invention is to develop an artificial synthesis system of various peptides having an azole derivative structure, develop a library of such peptides, and the like.

Solution to Problem

With a view to achieving the above-described object, the present inventors tried to introduce an azoline structure into a peptide by using PatD according to the method of Patent Document 1 and then convert the azoline structure into an azole structure by using PatG. Conversion from an azoline structure into an azole structure was however not observed in vitro system.

Since PatG converts only Cys-derived thiazoline into thiazole and thus has substrate specificity as its essential catalytic function, it cannot convert Ser- and Thr-derived azoline structures into an azole structure and therefore disadvantageously lacks versatility.

The present inventors therefore introduced an azoline derivative structure into a substrate peptide having a cassette region including a predetermined unnatural amino acid by using PatD and then performed a chemical structure-converting reaction. As a result, it has been confirmed that various azoline derivative structures of the peptide can be converted into an azole derivative structure, leading to the completion of the present invention.

The present invention relates to:

[1] a method of producing a peptide having, in the backbone thereof, an azole derivative structure, comprising the steps of:

synthesizing a substrate peptide of an azoline structure introducing enzyme having, in a modified region thereof, at least any one of the following amino acids;

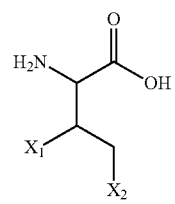

[Chemical formula 1]

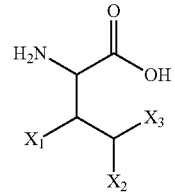

[Chemical formula 2]

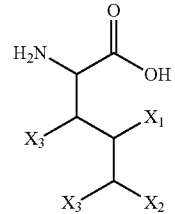

[Chemical formula 3]

-continued

[Chemical formula 4]

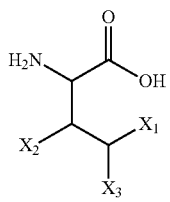

[in any of the compounds, $X_1$ represents a group selected from the group consisting of SH, OH, $NH_2$, $SR^1$, $OR^1$, $NHR^1$, and $N_3$ ($R^1$ represents a protecting group), $X_2$ represents an easily eliminable group; and $X_3$ represents hydrogen or a substituted or unsubstituted alkyl or aryl group having from 1 to 10 carbon atoms];

reacting the substrate peptide with an azoline structure introducing enzyme to obtain a peptide having an azoline derivative structure; and converting the azoline derivative structure of the resulting peptide into an azole derivative structure by inducing $HX_2$ elimination reaction of $X_2$ group;

[2] the method as described above in [1], wherein $X_2$ is a group selected from the group consisting of Cl, Br, I, OTs, OMs, and $N^+R^2{}_3$ ($R^2$ is independently selected from hydrogen or a substituted or unsubstituted alkyl or aryl group having from 1 to 10 carbon atoms);

[3] the method as described above in [1], wherein the amino acid is represented by the following formula:

[Chemical formula 5]

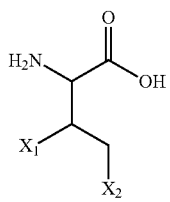

[wherein, $X_1$ represents OH and $X_2$ represents Cl, Br, or I];

[4] the method as described above in any one of [1] to [3], wherein the elimination reaction is performed at pH>9;

[5] the method as described above in any one of [1] to [4], wherein the elimination reaction is performed at 80° C. or more;

[6] the method as described above in any one of [1] to [5], further comprising a step of macrocyclizing the peptide;

[7] the method as described above in any one of [1] to [6], wherein the substrate peptide does not contain a leader sequence;

[8] the method as described above in any one of [1] to [7], wherein the substrate peptide further contains, in the modified region thereof or in a region other than the modified region, at least one non-protein amino acid;

[9] a method of constructing a peptide library having an azole derivative structure, comprising the steps of:

constructing an mRNA library encoding a substrate peptide library including two or more substrate peptides of an azoline structure introducing enzyme different in sequence of a modified region, the substrate peptides each containing, in the modified region thereof, at least any one of the following amino acids:

[Chemical formula 6]

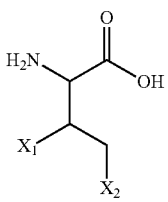

[Chemical formula 7]

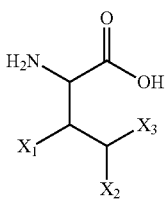

[Chemical formula 8]

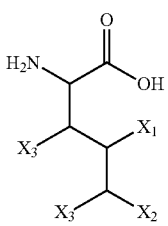

[Chemical formula 9]

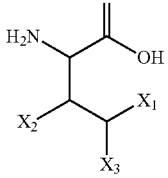

[in any of the compounds, $X_1$ represents a group selected from the group consisting of SH, OH, $NH_2$, $SR^1$, $OR^1$, $NHR^1$, and $N_3$ ($R^1$ represents a protecting group), $X_2$ represents an easily eliminable group; and $X_3$ represents hydrogen or a substituted or unsubstituted alkyl or aryl group having from 1 to 10 carbon atoms];

translating the mRNA library in a cell-free translation system to obtain a substrate peptide library;

reacting the substrate peptide library with an azoline structure introducing enzyme to obtain a peptide library having an azoline derivative structure; and obtaining a peptide library having an azole derivative structure by inducing an elimination reaction of $X_2$ group and thereby converting the azoline derivative structure of the peptide library having an azoline derivative structure into an azole derivative structure;

[10] the method as described above in [9], wherein $X_2$ is a group selected from the group consisting of Cl, Br, I, OTs, OMs, and $N^+R^2{}_3$ ($R^2$ is independently selected from hydrogen or a substituted or unsubstituted alkyl or aryl group having from 1 to 10 carbon atoms);

[11] the method as described above in [9], wherein the amino acid is represented by the following formula:

[Chemical formula 10]

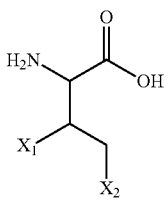

[wherein, $X_1$ represents OH and $X_2$ represents Cl, Br, or I];

[12] the method as described above in any one of [9] to [11], wherein the elimination reaction is performed at pH>9;

[13] the method as described above in any one of [9] to [12], wherein the elimination reaction is performed at 80° C. or more;

[14] the method as described above in any one of [9] to [13], further comprising a step of macrocyclizing the peptide;

[15] the method as described above in any one of [9] to [14], wherein the substrate peptide does not contain a leader sequence and the azoline structure introducing enzyme has a leader sequence bound thereto;

[16] the method as described above in any one of [9] to [15], wherein the substrate peptide further contains, in the modified region thereof or in a region other than the modified region, at least one non-protein amino acid;

[17] the method as described above in any one of [9] to [16], wherein the step of constructing an mRNA library comprises a step of binding puromycin to the 3' end of each mRNA of the mRNA library, and
an mRNA-bound substrate peptide library is obtained in the step of obtaining a substrate peptide library;

[18] a screening method for identifying a peptide having an azole derivative structure that binds to a target substance, comprising the steps of:
bringing a peptide library having an azole derivative structure constructed by the method as described above in any one of [9] to [17] into contact with the target substance, followed by incubation; and
selecting a peptide having an azole derivative structure that has bound to the target substance;

[19] a screening method for identifying a peptide having an azole derivative structure that binds to a target substance, comprising the steps of:
bringing an mRNA-bound peptide library having an azole derivative structure constructed by the method as described above in [17] into contact with the target substance, followed by incubation;
collecting an mRNA-bound peptide cluster having an azole derivative structure that has bound to the target substance;
obtaining, from an mRNA portion of the corrected mRNA-bound peptide cluster, a cDNA cluster by a reverse transcription reaction;
binding puromycin to the 3' end of the cDNA cluster, followed by translation to obtain an mRNA-bound peptide library; and
performing the above-described steps at least once to enrich the peptide having an azole derivative structure that binds to a target substance; and

[20] a screening method for identifying a peptide having an azole derivative structure that binds to a target substance, comprising the steps of:
obtaining, from an mRNA-bound peptide library having an azole derivative structure constructed by the method as described above in [17], a DNA-bound peptide library having an azole derivative structure by a reverse transcription reaction;
bringing the DNA-bound peptide library having an azole derivative structure into contact with the target substance, followed by incubation;
collecting a DNA-bound peptide cluster having an azole derivative structure that has bound to the target substance and amplifying a DNA portion of the cluster;
binding puromycin to the 3' end of the amplified DNA cluster, followed by translation to obtain an mRNA-bound peptide library; and
performing the above-described steps at least once to enrich a peptide having an azole derivative structure that binds to the target substance.

Advantageous Effects of Invention

By the method of the present invention, not only an azoline structure derived from Cys but also various azoline derivative structures can be converted into an azole derivative structure. This enables construction of an azole peptide library rich in diversity so that screening using this library can drastically enhance the possibility of obtaining an azole peptide having improved peptidase resistance, excellent binding ability to a target, high affinity for metals or nucleic acids, and improved biomembrane permeability.

BRIEF DESCRIPTION OF DRAWINGS

FIG. 8 shows MALDI-TOF-MS analysis results of the mass of the azoline-derivative-structure-introduced peptide after reaction at 95° C. for 30 minutes at pH 7.5, 9 or 10 in the presence of $Ag^+$.

DESCRIPTION OF EMBODIMENTS

Figure 1:
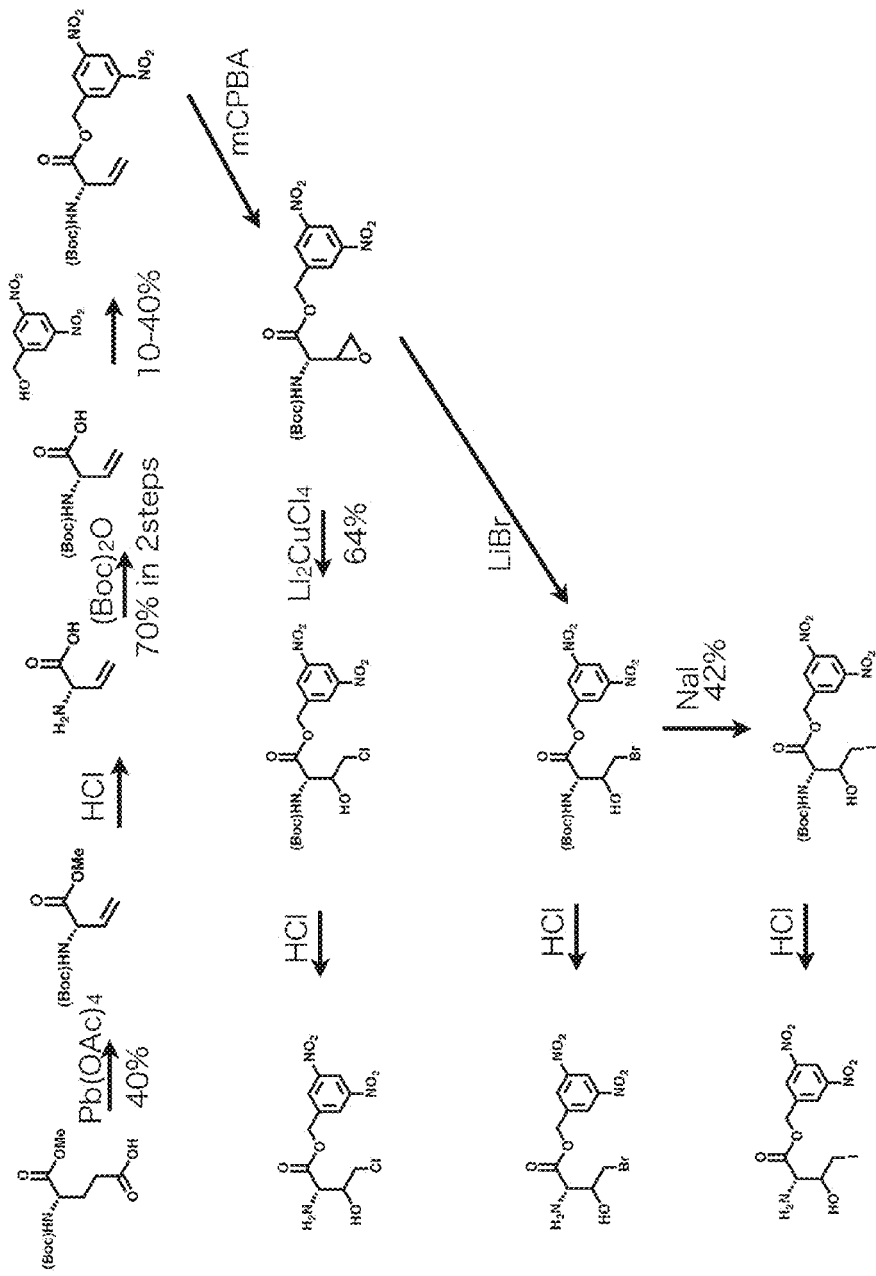
FIG. 1 schematically shows preparation steps of Cl-Thr-DBE, Br-Thr-DBE, and I-Thr-DBE.

The present invention provides a method of producing a peptide having an azole derivative structure. The term "peptide having an azole derivative structure" (which may hereinafter be called "azole peptide") as used herein means a peptide having, in the backbone structures thereof, at least one of the following azole structure and derivatives thereof (I) to (III). In the formulas, X represents S, O, or NH.

[Chemical formula 11]

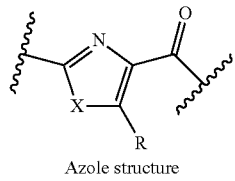

Azole structure

[Chemical formula 12]

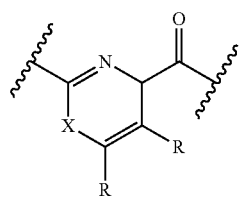

Azole derivative structure (I)

[Chemical formula 13]

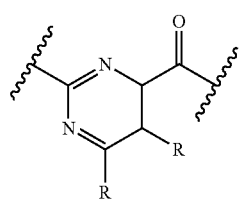

Azole derivative structure (II)

[Chemical formula 14]

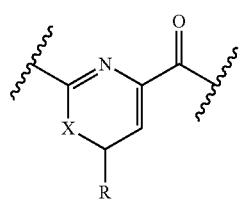

Azole derivative structure (III)

(Synthesis of Substrate Peptide of Azoline Structure Introducing Enzyme)

The method of producing an azole peptide according to the present invention comprises a step of synthesizing a substrate peptide of an azoline structure introducing enzyme containing, in a modified region thereof, at least any one of the following amino acids (I) to (IV):

[Chemical formula 15]

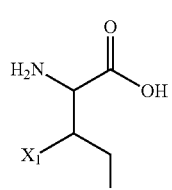

Amino acid (I)

[Chemical formula 16]

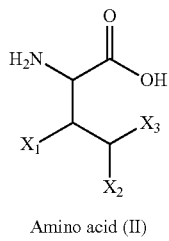

Amino acid (II)

[Chemical formula 17]

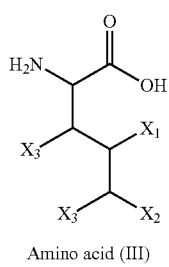

Amino acid (III)

[Chemical formula 18]

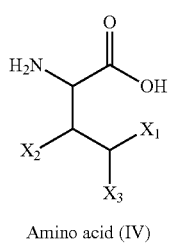

Amino acid (IV)

[in any of the compounds, $X_1$ represents a group selected from the group consisting of SH, OH, $NH_2$, $SR^1$, $OR^1$, $NHR^1$, and $N_3$ ($R^1$ represents a protecting group), $X_2$ represents an easily eliminable group; and $X_3$ represents hydrogen or a substituted or unsubstituted alkyl or aryl group having from 1 to 10 carbon atoms].

The term "azoline structure introducing enzyme" as used herein means an enzyme that introduces the above-described azoline derivative structure into the Cys residue, Ser residue, or Thr residue of a substrate peptide, a derivative thereof, or the like and it includes PatD and an enzyme having homology therewith. As the enzyme having homology with PatD, those included in, for example, the report of Lee, et al. (Lee, S. W. et al., PNAS vol. 105, No. 15, 5879-5884, 2008) can be used, but it is not limited to them. The azoline structure introducing enzyme may be a variant thereof insofar as it has azoline derivative structure introducing activity.

The term "substrate peptide of an azoline structure introducing enzyme" as used herein means a peptide that can be a substrate of an azoline structure introducing enzyme and permits introduction, into any of amino acid residues thereof, of an azoline derivative structure.

The "modified region" of the substrate peptide of an azoline structure introducing enzyme in the present invention is also called "cassette region" and it corresponds to a hypervariable region of a natural PatE peptide. As shown in Patent Document 1, the region can have an arbitrary sequence composed of from 2 to 40 amino acids. The number of amino acids in the modified region may be, for example, 2 or more and not more than 10, 12, 14, 16, 18, 20, 30, or 40.

The substrate peptide of an azoline structure introducing enzyme contains, in the modified region thereof, at least one of the above-described amino acids (I) to (IV). Two or more of the amino acids (I) to (IV) may be contained in the modified region. When two or more amino acids are contained, they may be the same or different amino acids and they may be adjacent to or separated from each other.

As shown in Patent Document 1, an amino acid residue to be modified by the azoline structure introducing enzyme may be contained in any site of the modified region so that the amino acids (I) to (IV) may be placed at any site of the modified region. For example, the amino acids (I) to (IV) may be placed at an even-numbered position from the N terminal of the modified region. The amino acids (I) to (IV) may also be placed so as not to be adjacent, on the side of the N terminal side thereof, to a hydrophilic amino acid (Asp, Glu, Arg, Lys, Asn, or Gln, or a hydrophilic derivative thereof).

In the amino acids (I) to (IV), $X_1$ represents a group selected from the group consisting of SH, OH, $NH_2$, $SR^1$, $OR^1$, $NHR^1$, and $N_3$. $R^1$ represents a protecting group. The protecting group can be selected as needed from protecting groups known to those skilled in the art. Examples of a protecting group of a hydroxyl group include a methyl group, a benzyl group, a p-methoxybenzyl group, a tert-butyl group, a trialkylsilyl group such as a trimethylsilyl group, a methoxymethyl group, a tetrahydropyranyl group, and an o-nitrobenzyl group; those of a protecting group of an amino group include a t-butoxycarbonyl group (Boc), a benzyloxycarbonyl group (Cbz), a fluorenylmethyloxycarbonyl group (Fmoc), an o-nitrobenzoyl group, and a pentenoyl group; those of a protecting group of a thiol group include a t-butyl group, a disulfide protecting group such as a hydroxyethylsulfide group, and a triphenylmethyl group. The protecting group is not limited thereto. When the amino acids (I) to (IV) contain $R^1$, deprotection follows the step of synthesizing a substrate peptide but before reaction between the substrate peptide and the azoline structure introducing enzyme. Deprotection may be performed as needed by those skilled in the art, depending on the kind of the protecting group.

In the amino acids (I) to (IV), $X_2$ is not particularly limited insofar as it is easily eliminable by appropriate chemical treatment and it may be selected as needed by those skilled in the art. Examples of $X_2$ include Cl, Br, I, F, a tosyl group (OTs), a mesyl group (Oms), a diazonium group ($N_2^+$), a trifluoromethanesulfonic group ($OSO_2CF_3$), and $N^+R^2{}_3$. Three $R^2$s of the $N^+R^2{}_3$ may be selected independently from hydrogen or substituted or unsubstituted alkyl or aryl groups having from 1 to 10 carbon atoms. The number of carbon atoms may be any of 1, 2, 3, 4, 5, 6, 7, 8, 9, and 10. Examples of the substituent include, but not limited to, a halogen atom, a cyano group, a hydroxy group, a nitro group, an amino group, an alkyl group, an aryl group, an alkene group, an alkyne group, and an azide group.

In the amino acids (I) to (IV), $X_3$ may be selected independently from hydrogen or substituted or unsubstituted alkyl or aryl groups having from 1 to 10 carbon atoms. The number of carbon atoms may be any of 1, 2, 3, 4, 5, 6, 7, 8, 9, and 10. Examples of the substituent include, but not limited to, a halogen atom, a cyano group, a hydroxy group, a nitro group, an amino group, an alkyl group, an aryl group, an alkene group, an alkyne group, and an azide group.

Specific examples of the amino acids (I) to (IV) include halothreonine which is an amino acid (I) having OH as $X_1$ and Cl, Br, or I as $X_2$.

In one mode, the substrate peptide of an azoline structure introducing enzyme has, similar to natural PatE, a leader sequence, a recognition sequence 1, a modified region, and a recognition sequence 2 in order of mention from the N terminal.

The leader sequence has, in the natural PatE, the following amino acid sequence:

(SEQ. ID NO: 1)
MNKKNILPQQGQPVIRLTAGQLSSQLAELSEEALGDA

Also in the substrate peptide of an azoline structure introducing enzyme in the present invention, this sequence may be used as the leader sequence.

As shown in Patent Document 1, PatD can introduce an azoline structure into a substrate peptide even when a sequence different from the leader sequence of PatE which is conventionally known as the leader sequence is used. Examples of such a sequence include MKEQNSFNLLQEV-TESELDLILGA (SEQ ID NO: 2) derived from another peptide (Lacticin 481 precursor), MILASLSTFQQM-WISKQEYDEAGDA (SEQ ID NO: 3) derived from human actin, and MELQLRPSGLEKKQAPISELNIAQTQGGD-SQVLALNA (SEQ ID NO: 4) obtained by shuffling the leader sequence of PatE.

Also in the substrate peptide of an azoline structure introducing enzyme in the present invention, although the leader sequence is not particularly limited insofar as the azoline derivative structure is introduced into the substrate peptide, the above-described sequences may be used.

The leader sequence may be composed of four or more, five or more, or six or more consecutive amino acids of the above-described sequences.

As shown in Patent Document 1, the leader sequence may not be included in the substrate peptide. In one mode, therefore, the substrate peptide of an azoline structure introducing enzyme may be a peptide having, the recognition sequence 1, a modified region, and the recognition sequence 2 in order from the N terminal.

In this case, a peptide having the leader sequence may be added as an independent peptide when the substrate peptide is reacted with the azoline structure introducing enzyme. Alternatively, the leader sequence may be bound to the azoline structure introducing enzyme in advance. In this case, the leader sequence may be bound to any position of the azoline structure introducing enzyme, but it is bound preferably to the N terminal. The leader-sequence-bound azoline structure introducing enzyme can be prepared by a known method or a method based thereon. For example, it can be prepared by synthesizing a nucleic acid encoding it and then allowing it to express as a fused peptide by using *Escherichia coli* or the like.

The recognition sequences 1 and 2 are sequences recognized by an azoline structure introducing enzyme composed of from 0 to 10 amino acids and they may be any sequence insofar as the azoline structure introducing enzyme recognizes it and introduces an azoline derivative structure. When the azoline structure introducing enzyme is PatD, for example, G(A/L/V)(G/E/D)(A/P)(S/T/C) (SEQ ID NO: 5) can be used as the recognition sequence 1 and it may be, for example, GLEAS (SEQ ID NO: 6). As the recognition sequence 2 by the azoline structure introducing enzyme, a sequence including (A/S)Y(D/E)G(A/L/V) (SEQ ID NO: 7) can be used. For example, it may be AYDGVEPS (SEQ ID NO: 8), AYDGV (SEQ ID NO: 9), AYDGVGSGSGS (SEQ ID NO: 10), AYDGVGGGGGG (SEQ ID NO: 11), or AYDGVEGSGSGS (SEQ ID NO: 12), or a sequence such as GGGGG (SEQ ID NO: 13), QQQQQ (SEQ ID NO: 14), LLLLL (SEQ ID NO: 15), or PPPPP (SEQ ID NO: 16) may be used.

As shown in Patent Document 1, a peptide having either one or neither of the recognition sequence 1 and the recognition sequence 2 may serve as a substrate of an azoline structure introducing enzyme so that the recognition sequences 1 and 2 are arbitrary constituents of the substrate peptide.

In one mode, the substrate peptide of an azoline structure introducing enzyme may have a linker sequence between the leader sequence and the recognition sequence 1, the recognition sequence 1 and the modified region, or the modified region and the recognition sequence 2.

In one mode, the substrate peptide of an azoline structure introducing enzyme may have two or more modified regions. When the substrate peptide has two modified regions, it may have, for example, the leader sequence, the recognition sequence 1, a modified region 1, the recognition sequence 2, a modified region 2, and a recognition sequence 3 in order from the N terminal.

In the present specification, the term "amino acid" is used in its broadest meaning and it embraces not only natural amino acids but also derivatives thereof and artificial amino acids. Examples of the amino acid used herein include natural protein L-amino acids, unnatural amino acids, and chemically synthesized compounds having properties known in the art as characteristics of an amino acid. Examples of the unnatural amino acids include, but not limited to, α,α-disubstituted amino acids (such as α-methylalanine), N-alkyl-α-amino acids, D-amino acids, β-amino acids, and α-hydroxy acids, each having a backbone structure different from that of natural amino acids; amino acids (such as norleucine and homohistidine) having a side-chain structure different from that of natural amino acids; amino acids (such as "homo" amino acids, homophenylalanine, and homohistidine) having extra methylene in the side chain thereof; and amino acids (such as cysteic acid) obtained by substituting a carboxylic acid functional group in the side chain by a sulfonic acid group.

In the present specification, the amino acids may be represented by a commonly used single-letter or three-letter code. Amino acids represented by a single-letter code or a three-letter code may each contain a variant or derivative thereof.

The substrate peptide may further contain, in a modified region thereof or a region other than the modified region, a non-protein amino acid. Examples of such a non-protein amino acid include, but not limited to, the following ones.

TABLE 1

| Initiator amino acids | |
|---|---|
| Acetyl-L-alanine | DBE |
| Acetyl-L-phenylalanine | CME |
| Acetyl-L-tyrosine | CME |
| Acetyl-L-tryptophan | CME |
| Acetyl-D-alanine | DBE |
| Acetyl-D-phenylalanine | CME |
| Acetyl-D-tyrosine | CME |
| Acetyl-D-tryptophan | CME |
| N-Chloroacetyl-L-alanine | DBE |
| N-Chloroacetyl-L-phenylalanine | CME |
| N-Chloroacetyl-L-tyrosine | CME |
| N-Chloroacetyl-L-tryptophan | CME |
| N-Chloroacetyl-D-alanine | DBE |
| N-Chloroacetyl-D-phenylalanine | CME |
| N-Chloroacetyl-D-tyrosine | CME |

TABLE 1-continued

| Initiator amino acids | |
|---|---|
| N-Chloroacetyl-D-tryptophan | CME |
| N-3-chloromethylbenzoyl-L-tyrosine | CME |
| N-3-chloromethylbenzoyl-L-tryptophane | CME |

TABLE 2

| Amino acids that crosslink in peptides | |
|---|---|
| Nγ-(2-chloroacetyl)-α,γ-diaminobutylic acid | DBE |
| Nγ-(2-chloroacetyl)-α,γ-diaminopropanoic acid | DBE |

TABLE 3

| D-amino acids | |
|---|---|
| D-Serine | DBE |
| D-Phenylalanine | CME |
| D-Tyrosine | CME |
| D-Tryptophan | CME |

TABLE 4

| N-methylamino acids | |
|---|---|
| N-methyl-Glycine | DBE |
| N-methyl-Alanine | DBE |
| N-methyl-Serine | DBE |
| N-methyl-Histidine | DBE |
| N-methyl-Phenylalanine | CME |
| N-methyl-Tyrosine | CME |
| N-methyl-Tryptophan | CME |

TABLE 5

| Peptoid blocks | |
|---|---|
| N-ethyl-Glycine | DBE |
| N-n-propyl-Glycine | DBE |
| N-n-butyl-Glycine | DBE |
| N-n-pentyl-Glycine | DBE |
| N-n-hexyl-Glycine | DBE |
| N-n-heptyl-Glycine | DBE |
| N-n-octyl-Glycine | DBE |
| N-isopentyl-Glycine | DBE |
| N-(2-phenylethyl)-Glycine | CME |
| N-(3-phenylpropyl)-Glycine | CME |
| N-[2-(p-hydroxyphenyl)ethyl]-Glycine | CME |

TABLE 6

| Other special amino acids | |
|---|---|
| p-biphenylalanine | CME |
| p-trifluoromethylphenylalanine | CME |
| p-azidophenylalanine | CME |
| p-biotinyl-aminophenylalanine | CME |
| e-N-Biotinyl-lysine | DBE |
| e-N-Acetyl-lysine | DBE |
| L-Citrulline | DBE |
| L-5-Hydroxytryptphan | CME |
| L-1,2,3,4,-Tetrahydroisoquinoline-3-carboxylic acid | DBE |
| Aminoisobutyric acid | DBE |
| N-methyl-aminoisobutyric acid | DBE |
| N-methyl-Phenylglycine | CME |

The synthesis method of the "substrate peptide of an azoline structure introducing enzyme" is not particularly limited and usable is a known method or a method based on it, for example, chemical synthesis method such as liquid phase method, solid phase method, and hybrid method using liquid phase method and solid phase method in combination, genetic recombination method, or synthesis in a cell-free translation system.

For example, the substrate peptide can be obtained by preparing a nucleic acid encoding the substrate peptide and then translating/synthesizing the nucleic acid in a cell-free translation system. The nucleic acid encoding the substrate peptide can be designed as needed by those skilled in the art by using a genetic code used in vivo translation system, a reprogrammed genetic code, or a combination of them. The "nucleic acid" in the present specification may be either DNA or RNA.

By using a cell-free translation system and an artificial aminoacyl RNA catalyst flexizyme (Flexizyme) developed by the present inventors, a genetic code made of mRNA triplet can be reprogrammed so as to encode an amino acid different from that in a vivo translation system (WO2008/059823) so that unnatural amino acids (I) to (IV) may be incorporated into a peptide by translation. This will hereinafter be described in detail.

Flexizyme (Flexizyme) is an artificial RNA catalyst (RNA catalyst having acyl tRNA synthetase-like activity) capable of linking (acylating) an arbitrary amino acid or hydroxy acid to an arbitrary tRNA. In a reconstituted translation system, using flexizyme instead of aminoacyl tRNA synthesized using a natural aminoacyl tRNA synthetase, a desired amino acid or hydroxy acid can be allowed to correspond to an arbitrary codon different from that of a natural genetic code.

As flexizyme, for example, those described in the following documents are known: H. Murakami, H. Saito, and H. Suga, (2003), Chemistry & Biology, Vol. 10, 655-662; H. Murakami, D. Kourouklis, and H. Suga, (2003), Chemistry & Biology, Vol. 10, 1077-1084; H. Murakami, A. Ohta, H. Ashigai, H. Suga (2006) Nature methods 3, 357-359; N. Niwa, Y. Yamagishi, H. Murakami, H. Suga, (2009) Bioorganic & Medicinal Chemistry Letters 19, 3892-3894; and WO2007/066627 "Multi-purpose acylation catalyst and use thereof". As flexizyme, original flexizyme (Fx) and altered ones thereof such as dinitrobenzyl flexizyme (dFx), enhanced flexizyme (eFx), and aminoflexizyme (aFx) are also known.

The method of linking an arbitrary amino acid with an arbitrary tRNA is not limited to a method using flexizyme and another method can also be used in the present invention.

For genetic code reprogramming, usable is a translation system in which only necessary components which have remained after free removal of the constituting components from the translation system according to the purpose can be reconstituted. For example, when a translation system is reconstituted after removal of a specific amino acid, the codon corresponding to the amino acid becomes a vacant codon. An arbitrary amino acid is then linked to a tRNA having an anticodon complementary to the vacant codon by making use of a flexizyme or the like and translation is performed by adding the resulting product. As a result, the arbitrary amino acid is encoded by the vacant codon and a peptide having the desired amino acid introduced therein instead of the removed amino acid is translated.

By this method, the amino acids (I) to (IV) or functional groups 1 and 2 for macrocyclization which will be described later can be assigned to an arbitrary codon and introduced into a peptide by translation.

As the cell-free translation system, an *Escherichia coli* extract or a wheat germ extract can be used. A rabbit reticulocyte extract or an insect cell extract may also be used. A reconstituted cell-free translation system obtained by reconstituting a ribosome protein, aminoacyl tRNA synthetase (ARS), ribosomal RNA, amino acid, rRNA, GTP, ATP, translation initiation factor (IF), elongation factor (EF), termination factor (RF), and ribosome regeneration factor (RRF), and another factor necessary for translation, which have been purified, may also be used.

A system including RNA polymerase may be used in order to simultaneously perform transcription from DNA. Examples of a commercially available cell-free translation system include *Escherichia-coli* derived systems such as RTS-100 (registered trade mark) of Roche Diagnostics, reconstituted translation systems such as PURESYSTEM (registered trademark) of PGI, PURExpressR In Vitro Protein Synthesis Kit of New England Biolabs, and systems using a wheat germ extract such as that of ZOEGENE Corporation or CellFree Sciences.

As a system using ribosome of *Escherichia coli*, the technology described, for example, in the following documents is known: H. F. Kung et al., 1977. The Journal of Biological Chemistry Vol. 252, No. 19, 6889-6894; M. C. Gonza et al., 1985, Proceeding of National Academy of Sciences of the United States of America Vol. 82, 1648-1652; M. Y. Pavlov and M. Ehrenberg, 1996, Archives of Biochemistry and Biophysics Vol. 328, No. 1, 9-16; Y. Shimizu et al., 2001, Nature Biotechnology Vol. 19, No. 8, 751-755; H. Ohashi et al., 2007, Biochemical and Biophysical Research Communications Vol. 352, No. 1, 270-276.

By the cell-free translation system, a high-purity product can be obtained without purifying an expression product.

(Reaction Between Substrate Peptide and Azoline Structure Introducing Enzyme)

The method of producing an azole peptide according to the present invention next comprises a step of reacting the substrate peptide with the azoline structure introducing enzyme to obtain a peptide having an azoline derivative structure.

The term "peptide having an azoline derivative structure" (which may also be called "azoline peptide" as used herein means a peptide having, in the backbone structure thereof, at least one of the following azoline structure and a derivative thereof. In the formula, X represents S, O, or NH.

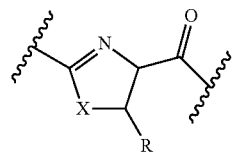

[Chemical formula 19]

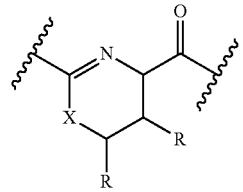

[Chemical formula 20]

The azoline structure introducing enzyme to be used in this step may be obtained by extraction/purification from a microorganism that produces the enzyme or by expression using gene recombination. The enzyme may be a variant thereof insofar as it introduces an azoline derivative structure.

The reaction between the substrate peptide and the azoline structure introducing enzyme may be performed by adding the azoline structure introducing enzyme to the substrate peptide in the vessel in which the substrate peptide has been expressed, that is, in one pot, without purifying the substrate peptide; or may be reacted with the azoline structure introducing enzyme after purifying the substrate peptide in another vessel.

The reaction between the substrate peptide and the azoline structure introducing enzyme, for example, when the azoline structure introducing enzyme is PatD, can be performed under the conditions selected as needed by those skilled in the art within a range of a final concentration of from 0.1 μM to 50 μm, a reaction temperature of from 4° C. to 45° C., and a reaction time of from 5 minutes to 100 hours.

When the substrate peptide does not contain a leader sequence, the substrate peptide may be reacted with a leader-sequence-bound azoline structure introducing enzyme. When the substrate peptide does not contain a leader sequence and at the same time, the azoline structure introducing enzyme has no leader sequence bound thereto, a leader sequence may be added to the reaction system as an independent peptide in this step.

By the reaction with the azoline structure introducing enzyme, the azoline structure is introduced into the residue(s) of the amino acids (I) to (IV) of the substrate peptide. Whether or not the azoline derivative structure has been introduced can be verified, for example, by MALDI-TOF-MS analysis of a mass change.

(Conversion of Azoline Derivative Structure into Azole Ring)

The method of producing an azole peptide according to the present invention comprises next a step of inducing an elimination reaction of $X_2$ group in the peptide having the azoline derivative structure to convert the azoline derivative structure into an azole derivative structure.

Although the elimination reaction condition in the present specification is not particularly limited insofar as the azoline derivative structure is converted into an azole derivative structure, it may be set at pH>9. Examples include pH=about 9.5 or more, pH=about 10 or more, pH=about 10.5 or more, pH=about 11 or more, and pH=about 11.5 or more.

Basic conditions can be adjusted by adding, for example, a basic solution (for example, KOH) or a basic buffer.

Although the temperature during the elimination reaction is also not particularly limited insofar as the azoline derivative structure is converted into an azole derivative structure, examples include about 60° C. or more, about 65° C. or more, about 70° or more, about 75° C. or more, about 80° C. or more, about 85° C. or more, about 90° C. or more, about 95° C. or more, and about 98° C. or more.

Although the reaction time can also be selected as needed by those skilled in the art, examples include 10 minutes or more, 20 minutes or more, 30 minutes or more, 40 minutes or more, 50 minutes or more, 60 minutes or more, and 70 minutes or more.

After isomerization of a double bond formed by elimination in the elimination reaction of $X_2$, an azole derivative structure is formed at the site of the amino acids (I) to (IV). In the method of the present invention, the azole derivative structure is introduced by such a non-enzymatic method so that conversion into the azole derivative structure can yield not only Cys-derived thiazoles but also various azole peptides.

Whether or not the azoline derivative structure has been converted into an azole ring can be verified, for example, by MALDI-TOF-MS analysis of a mass change.

(Macrocyclization)

The method of producing an azole peptide in the present invention may further comprise a step of macrocyclizing the azole peptide.

Although the macrocyclization method is not particularly limited, macrocyclization is performed, for example, by introducing, into the azole peptide, an amino acid having the below-described functional group 1 and an amino acid having a functional group 2 corresponding thereto. Either the functional group 1 or the functional group 2 may be placed on the N-terminal side. For example, an azole peptide containing, in the macrocyclic portion thereof, the azole derivative structure can be obtained by placing the functional group 1 on the N terminal side of the modified region in the azole peptide and placing the functional group 2 on the C terminal side.

TABLE 7

| | Functional group 1 | | Functional group 2 | |
|---|---|---|---|---|
| (A) | —C(=O)—CH$_2$—X$_1$ | (A-1) | HS— | (A-2) |
| (B) | —C≡C—H | (B-1) | N$_3$— | (B-2) |
| (C) | —Ar—CH$_2$NH$_2$ | (C-1) | HO-(indole ring) | (C-2) |
| (D) | —C≡C—CH$_2$—X$_1$ | (D-1) | HS— | (D-2) |
| (E) | —Ar—CH$_2$—X$_1$ | (E-1) | HS— | (E-2) |

In the above formulas, $X_1$ represents Cl, Br, or I and Ar represents a substituted or unsubstituted aromatic ring.

As the amino acid having a functional group of (A-1), for example, a chloroacetylated amino acid can be used. Examples of the chloroacetylated amino acid include N-chloroacetyl-L-alanine, N-chloroacetyl-L-phenylalanine, N-chloroacetyl-L-tyrosine, N-chloroacetyl-L-tryptophan, N-3-(2-chloroacetamido)benzoyl-L-phenylalanine, N-3-(2-chloroacetamido)benzoyl-L-tyrosine, N-3-(2-chloroacetamido)benzoyl-L-tryptophane, β-N-chloroacetyl-L-diaminopropanoic acid, γ-N-chloroacetyl-L-diaminobutyric acid, σ-N-chloroacetyl-L-ornithine, and ε-N-chloroacetyl-L-lysine, and D-amino acid derivatives corresponding thereto.

Examples of amino acids having the functional group (A-2) include cysteine, homocysteine, mercaptonorvaline, mercaptonorleucine, 2-amino-7-mercaptoheptanoic acid, 2-amino-8-mercaptooctanoic acid, and amino acids obtained by protecting the SH group of these amino acids and then eliminating the protecting group, and D-amino acid derivatives corresponding thereto.

The cyclization method may be carried out according to the method described, for example, in Kawakami, T. et al., Nature Chemical Biology 5, 888-890 (2009); Yamagishi, Y. et al., ChemBioChem 10, 1469-1472 (2009); Sako, Y. et al., Journal of American Chemical Society 130, 7932-7934 (2008); Goto, Y. et al., ACS Chemical Biology 3, 120-129

(2008); and Kawakami T. et al, Chemistry & Biology 15, 32-42 (2008), and WO2008/117833.

As amino acids having the functional group (B-1), for example, propargylglycine, homopropargylglycine, 2-amino-6-heptynoic acid, 2-amino-7-octynoic acid, and 2-amino-8-nonynoic acid can be used. In addition, 4-pentynoylated or 5-hexynoylated amino acids can also be used. Examples of the 4-pentynoylated amino acids include N-(4-pentenoyl)-L-alanine, N-(4-pentenoyl)-L-phenylalanine, N-(4-pentenoyl)-L-tyrosine, N-(4-pentenoyl)-L-tryptophan, N-3-(4-pentynoylamido)benzoyl-L-phenylalanine, N-3-(4-pentynoylamido)benzoyl-L-tyrosine, N-3-(4-pentynoylamido)benzoyl-L-tryptophane, β-N-(4-pentenoyl)-L-diaminopropanoic acid, γ-N-(4-pentenoyl)-L-diaminobutyric acid, σ-N-(4-pentenoyl)-L-ornithine, and ε-N-(4-pentenoyl)-L-lysine, and D-amino acid derivatives corresponding thereto.

As amino acids having the functional group (B-2), for example, azidoalanine, 2-amino-4-azidobutanoic acid, azidoptonorvaline, azidonorleucine, 2-amino-7-azidoheptanoic acid, and 2-amino-8-azidooctanoic acid can be used. In addition, azidoacetylated or 3-azidopentanoylated amino acids can also be used. Examples of the azidoacetylated amino acids include N-azidoacetyl-L-alanine, N-azidoacetyl-L-phenylalanine, N-azidoacetyl-L-tyrosine, N-azidoacetyl-L-tryptophan, N-3-(4-pentynoylamido)benzoyl-L-phenylalanine, N-3-(4-pentynoylamido)benzoyl-L-tyrosine, N-3-(4-pentynoylamido)benzoyl-L-tryptophane, β-N-azidoacetyl-L-diaminopropanoic acid, γ-N-azidoacetyl-L-diaminobutyric acid, σ-N-azidoacetyl-L-ornithine, and ε-N-azidoacetyl-L-lysine, and D-amino acid derivatives corresponding thereto.

The cyclization method can be performed according to the method described, for example, in Sako, Y. et al., Journal of American Chemical Society 130, 7932-7934 (2008) or WO2008/117833.

Examples of amino acids having the functional group (C-1) include N-(4-aminomethyl-benzoyl)-phenylalanine ($_{AMB}$F) and 4-3-aminomethyltyrosine.

Examples of amino acids having the functional group (C-2) include 5-hydroxytryptophan ($W_{OH}$).

The cyclization method can be performed according to the method described, for example, in Yamagishi, Y. et al., ChemBioChem 10, 1469-1472 (2009) or WO2008/117833.

Examples of amino acids having the functional group (D-1) include 2-amino-6-chloro-hexynoic acid, 2-amino-7-chloro-heptynoic acid, and 2-amino-8-chloro-octynoic acid.

Examples of amino acids having the functional group (D-2) include cysteine, homocysteine, mercaptonorvaline, mercaptonorleucine, 2-amino-7-mercaptoheptanoic acid, and 2-amino-8-mercaptooctanoic acid, amino acids obtained by protecting the SH group of these amino acids and then eliminating the protecting group, and D-amino acid derivatives corresponding thereto.

The cyclization method can be performed according to the method described, for example, in WO2012/074129.

Examples of the amino acid having the functional group (E-1) include N-3-chloromethylbenzoyl-L-phenylalanine, N-3-chloromethylbenzoyl-L-tyrosine, and N-3-chloromethylbenzoyl-L-tryptophane, and D-amino acid derivatives corresponding thereto.

Examples of the amino acid having the functional group (E-2) include cysteine, homocysteine, mercaptonorvaline, mercaptonorleucine, 2-amino-7-mercaptoheptanoic acid, and 2-amino-8-mercaptooctanoic acid, and amino acids obtained by protecting the SH group of these amino acids and then eliminating the protecting group, and D-amino acid derivatives corresponding thereto.

The macrocyclization step is performed typically after conversion of the azoline derivative structure into an azole derivative structure, but may be performed in any stage after the step of synthesizing a substrate peptide of an azoline structure introducing enzyme.

(Cleaving of Leader Sequence)

In the method of producing an azole peptide in the present invention, when the substrate peptide contains the leader sequence, a step of cleaving the leader sequence may be performed. This step sometimes facilitates binding to a target substance because an extra portion is removed from the azole peptide.

Cleaving of the leader sequence may also be performed, for example, by adding a peptidase to the vessel in which the azoline structure introducing enzyme has been reacted.

Cleaving of the leader sequence may be performed at any site of the leader sequence, the recognition sequence 1, between the leader sequence and the recognition sequence 1, and between the recognition sequence 1 and the modified region. A peptidase is selected, depending on the sequence of the site to be cleaved. Examples of the peptidase include, but not limited to, trypsin, Glu-C, Lys-C, Asp-N, Lys-N, Arg-C, thrombin, Factor Xa, prescission protease, TEV protease, and enterokinase, and HRV 3C Protease.

As one example, when the substrate peptide contains GLEAS as the recognition sequence 1, endoproteinase Glu-C can be used for cleaving between Glu and Ala. Cleaving with Glu-C can be performed following a known method.

Cleaving of the leader sequence is performed typically after the step of converting the azoline derivative structure into an azole derivative structure. For example, after the step of converting the azoline derivative structure into an azole derivative structure and cleaving of the leader sequence, macrocyclization may be performed.

(Method of Constructing Azole Peptide Library)

The present invention embraces also a method of constructing an azole peptide library.

The term "azole peptide library" as used herein means a library including azole peptides different in sequence of a modified region.

The method of constructing an azole peptide library according to the present invention is started from construction of a library of substrate peptides of an azoline structure introducing enzyme. The substrate peptides are different in modified region and in addition, each modified region includes at least one of the amino acids (I) to (IV). A step of constructing a substrate peptide library includes a step of constructing an mRNA library encoding the substrate peptide library and a step of translating the mRNA library in a cell-free translation system to obtain the substrate peptide library.

Such an mRNA library can be constructed in a known manner by those skilled in the art (for example, Patent Document 1).

For example, when Met is removed from a reconstituted translation system, ATG encoding it becomes a vacant codon so that any of the amino acids (I) to (IV) can be assigned to the vacant codon. By constituting a portion of the substrate-peptide encoding mRNA that encodes the modified region from NNN, NNK, NNT, or NNG (N represents A, C, G, or T; K represents G or T) and ATG, a substrate peptide having a modified region that has a random sequence and includes any of the amino acids (I) to (IV) can be synthesized.

Alternatively, by constituting a portion of the substrate-peptide-encoding mRNA that encodes the modified region from NNN, NNK, NNT, or NNG and WST with WST (W represents A or T and S represents C or G) as a codon for the amino acids (I) to (IV), four unnatural amino acids can be introduced at random into the modified region and another amino acid in the modified region can be allowed to have a random sequence.

The other sequence of the mRNA library can be designed in consideration of the arrangement of the leader sequence, the recognition sequence, the protease recognition site for cleaving the leader sequence, and the functional groups 1 and 2 for macrocyclization.

The step of translating the mRNA library in a cell-free translation system to obtain the substrate peptide library, a step of reacting the substrate peptide library with an azoline structure introducing enzyme to obtain a peptide library having the azoline derivative structure, and a step of inducing an elimination reaction of $X_2$ group to convert the azoline derivative structure of the peptide library having an azoline derivative structure into an azole derivative structure and thereby obtaining a peptide library having the azole derivative structure can be performed based on the above-described method of producing an azole peptide.

In one mode, the method of constructing an azole peptide library according to the present invention is performed by, after the step of constructing an mRNA library encoding the substrate peptide library but before the translation step, binding puromycin to the 3' end of each mRNA of the mRNA library. Although the method of binding puromycin to each mRNA is not particularly limited, for example, a puromycin linker obtained by binding puromycin to a DNA capable of hybridizing to the sequence of the 3' end of each mRNA can be used.

As a result, by translating the mRNA library, an mRNA-substrate peptide complex library in which mRNA and the substrate peptide have been bound to each other can be obtained and by reacting the library with an azoline structure introducing enzyme and heating the product under basic conditions, an mRNA-azole peptide complex library in which mRNA and an azole peptide have been bound to each other can be obtained.

This method enables application of the azole peptide to mRNA display (Nemoto, N. et al., FEBS Lett. 1997, 405-408; Roberts, R. W. and Szostak, J. W. Proc. Natl. Acad. Sci. USA 1997, 94, 12297-12302).

(Screening Method)

The present invention also embraces a screening method for identifying an azole peptide that binds to a target substance by using an azole peptide library.

In one mode, the screening method of the present invention comprises a step of bringing an azole peptide library constructed by the method of the present invention into contact with a target substance, followed by incubation.

Although the "target substance" in the present specification is not particularly limited, examples of it include low molecular compounds, high molecular compounds, nucleic acids, peptides, proteins, sugars, and lipids. In particular, the method using the library of the present invention can be applied also to the case where the target substance is a protein having protease activity.

The target substance, after immobilized on a solid-phase support, can be brought into contact with the library of the present invention. Although in the present specification, the "solid-phase support" is not particularly limited insofar as it is a support on which the target substance can be immobilized, examples include microtiter plates, substrates, and beads made of glass, a metal, a resin, or the like, nitrocellulose membranes, nylon membranes, and PVDF membranes. The target substance can be immobilized on such a solid-phase support in a known manner.

The target substance and the library are brought into contact with each other in a buffer selected as needed and they are interacted while controlling pH, temperature, time, and the like.

The screening method of the present invention next comprises a step of selecting an azole peptide that has bound to the target substance, further. In binding to the target substance, for example, a peptide is labeled in advance by a known method that detectably labels a peptide and after the above-described incubation step, the surface of the solid-phase support is washed with a buffer to detect a compound that has bound to the target substance.

Examples of the detectable label include enzymes such as peroxidase and alkaline phosphatase, radioisotopes such as $^{125}$I, $^{131}$I, $^{35}$S, and $^{3}$H, fluorescent substances such as fluorescein isothiocyanate, rhodamine, dansyl chloride, phycoerythrin, tetramethyl rhodamine isothiocyanate, and near infrared fluorescent materials, light-emitting substances such as luciferase, luciferin, and aequorin, and nanoparticles such as gold colloid and quantum dot. When an enzyme is used as the label, a peptide can be detected by adding a substrate of the enzyme to develop a color. It can also be detected by binding biotin to a peptide and then binding avidin or streptavidin labeled with an enzyme or the like to the biotin-bound peptide.

It is possible not only to detect and analyze the presence or absence or degree of binding but also to analyze accelerated or inhibited activity of the target substance and thereby identify an azole peptide having such acceleration activity or inhibition activity. Such a method enables identification of a heterocyclic compound having physiological activity and useful as a drug.

Screening can be carried out using the mRNA-azole peptide complex library while applying the mRNA display method thereto.

For example, the mRNA-azole peptide complex library is brought into contact with a target substance immobilized on a solid-phase support. The mRNA-bound azole peptides bound to the target substance are collected and from the mRNA portion thereof, a cDNA cluster is obtained by a reverse transcription reaction. By amplifying the cDNA cluster as needed, binding puromycin to the 3' end of each cDNA, and translating it, an mRNA-azole peptide complex library can be obtained again. This library contains an mRNA-azole peptide complex having higher affinity for the target substance. By performing this step in repetition, an azole peptide having high affinity for the target substance can be obtained as a result of enrichment.

In another mode, the mRNA-azole peptide complex library is subjected to a reverse transcription reaction and then the library is brought into contact with a target substance immobilized on a solid-phase support. The complexes that bind to the target substance are collected and their DNA is amplified by PCR. The mRNA-azole peptide complex library constructed again by using the resulting DNA contains mRNA-azole peptide complexes having higher affinity for the target substance. By performing this step in repetition, an azole peptide having high affinity for the target substance can be obtained as a result of enrichment.

Since the base sequence of a cDNA obtained by the reverse transcription reaction of the enriched mRNA-azole peptide complex can be determined in a manner known per se in the art, the sequence of an azole peptide that binds to a target substance can be known easily.

(Screening Kit)

The present invention also provides a kit for screening an azole peptide library.

In one mode, the screening kit of the present invention includes the azole peptide library constructed by the production method of the present invention.

The screening kit of the present invention includes, in addition, a reagent and an apparatus necessary for detecting the binding between a target substance and an azole peptide. Examples of such a reagent and apparatus include, but not limited to, solid-phase supports, buffers, labeling reagents, enzymes, enzyme reaction terminator solutions, and microplate readers.

The disclosure of all the patent documents and non-patent documents cited herein are incorporated herein by reference in its entirety.

EXAMPLES

The present invention will hereinafter be described specifically based on Examples, but the present invention is not limited to or by them. The present invention can be changed into various modes by those skilled in the art without departing from the significance of the present invention. Such changes are also embraced in the scope of the present invention.

1. Preparation of DNA Encoding Substrate Peptide, and Translation/Synthesis of Substrate Peptide A DNA encoding a substrate peptide having the following amino acid sequence was prepared in a manner similar to that of Patent Document 1.

(SEQ ID NO: 17)
MNKKNILPQQGQPVIRLTAGQLSSQLAELSEEALGDAGLEASVXAYD
GVEPS.

X is an amino acid residue of the following formula in which $X_1$ is OH and $X_2$ is I.

[Chemical formula 21]

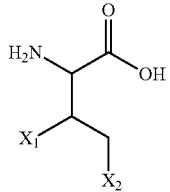

First, I-Thr-DBE was prepared (DBE=dinitro benzyl ester). It is schematically shown in FIG. 1. Then, according to the method of Goto et al. (Nat. Protocols 6, 779-790 (2011)), I-Thr was bound to tRNA by using Flexizyme. Binding was performed under the conditions under which 25 µM of Flexizyme, 25 µM of microhelix, 600 mM of $MgCl_2$, and 3 mM of I-Thr-DBE were used.

The substrate peptide was translated using a DNA having the following sequence: 5'-GGCGTAATACGACTCAC-TATAGGGTTAACTTTAACAAGGAGAAAAAC[AT GAACAAGAAAAACATCCTGCCCCAACAAGGT-CAACCGGTTATCCGCTTA ACCGCAGGACAGTT-GAGCTCGCAACTCGCCGAACTGTCTGAAGAAGCA CTGGGCGACGCGGGGTTGGAGGCAAGCGTT"TGT-"GCGTACGATGGCG TTGAGCCATCT]TAAGCTTCG-3' (SEQ ID NO: 18) 5'-CGAAGCTTAAGATGGCT-CAACGCCATCGTACGCACAAACGCTTGCCTC CAACCCCGCGTCGCCCAGTGCTTCTTCAGACAGT-TCGGCGAGTTGCGA GCTCAACTGTCCTGCGGT-TAAGCGGATAACCGGTTGACCTTGTTGGGG CAG-GATGTTTTTCTTGTTCATGTTTTTCTCCTTGTTAAA GTTAACCCTATA GTGAGTCGTATTACGCC-3' (SEQ ID NO: 19).

Of the sequence of the sense chain, the sequence in [ ] corresponds to a coding region, while the TGT codon in " " corresponds to a codon to which I-Thr has been assigned.

Next, according to the method of Kawakami et al. (Kawakami et al., Chemistry & Biology 15, 32-42 (2008)), transcription/translation was performed in a 5.0 µl scale cell-free protein expression system (37° C., 1 hour).

The peptide was desalted with Wash Buffer (4% MeCN, 0.5% AcOH, 95.5% $H_2O$) by using c-18 tip (Nikkyo Technos) and the desalted peptide was extracted using Elute Buffer (80% MeCN, 0.5% AcOH, 19.5% $H_2O$). The MALDI-TOF-MS analysis of the mass of the peptide thus extracted was performed using, as Matrix, α-cyano-4-hydroxycinnamic acid or sinapinic acid.

Figure 2:
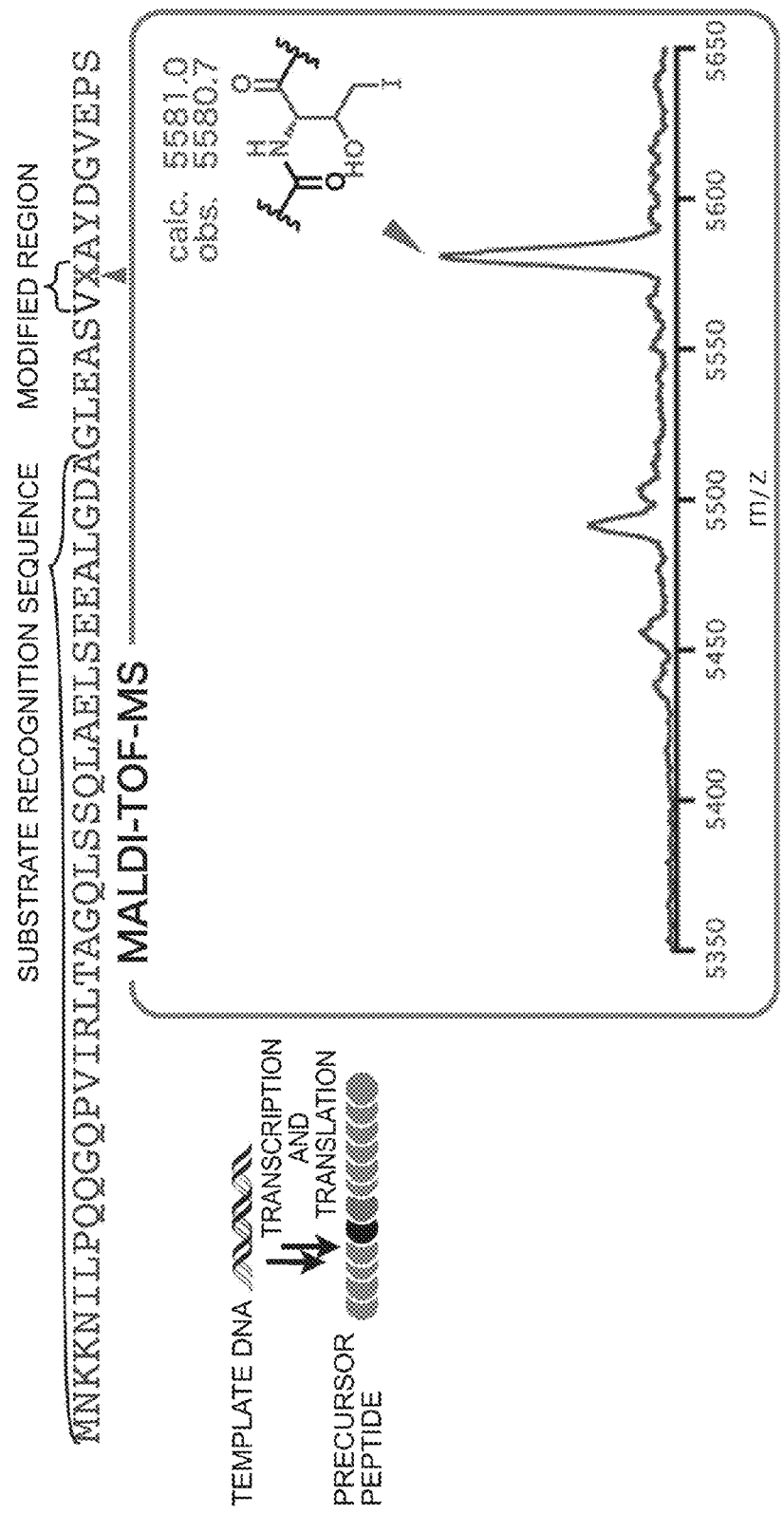
FIG. 2 shows MALDI-TOF-MS analysis results of the mass of a substrate peptide of PatD.

The results are shown in FIG. 2.

2. PatD Enzyme Reaction

To the reaction liquid (5 µL) obtained by the translation were added PatD, ATP, and DTT to give final concentrations of 6 µM, 0.5 µM, and 7.5 µM, respectively and a mixture having a total amount of 10 µL was obtained. The resulting mixture was reacted at 25° C. for 16 hours.

Figure 3:
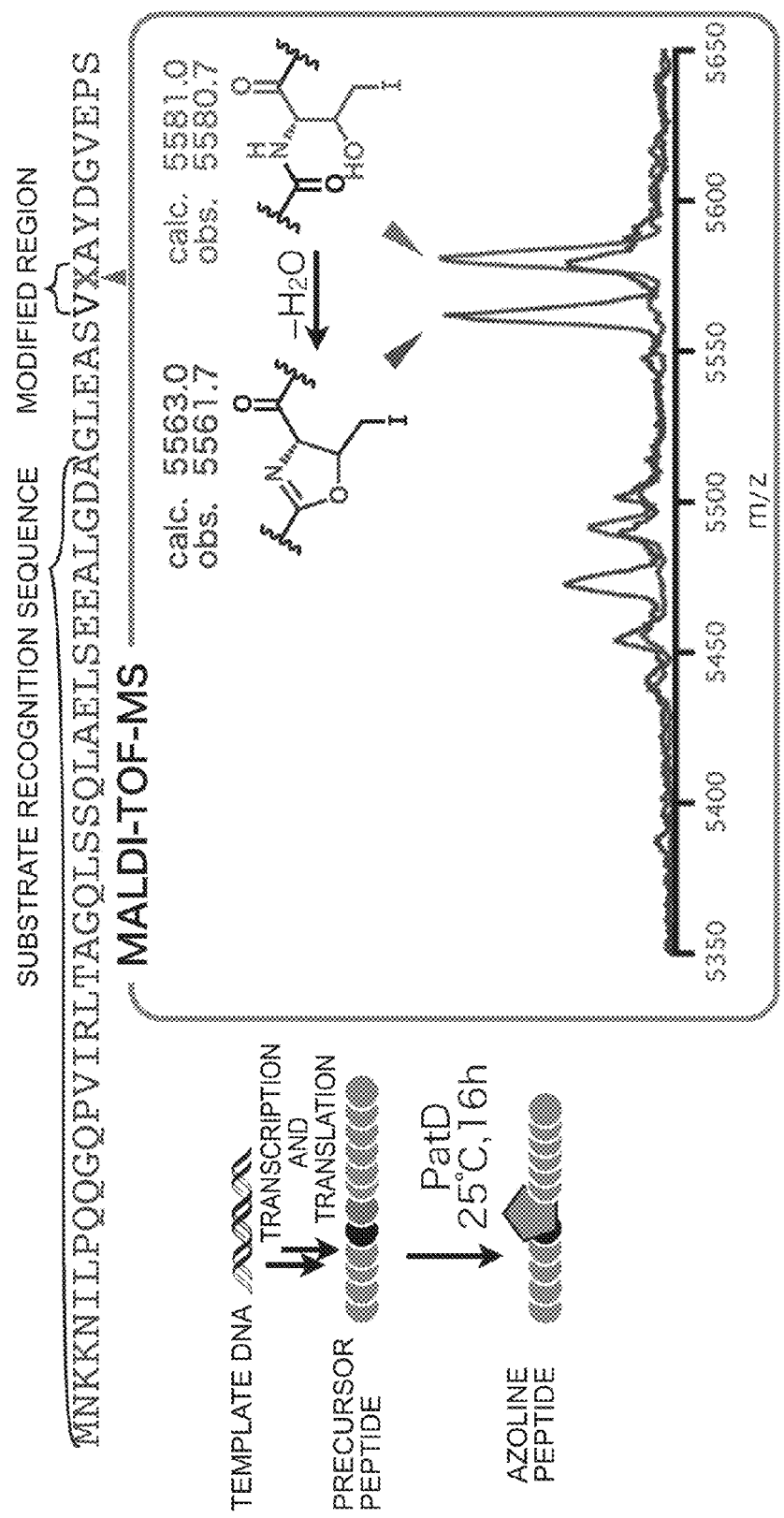
FIG. 3 shows MALDI-TOF-MS analysis results of the mass of an azoline-derivative-structure-introduced substrate peptide obtained by reaction with PatD.

The results of analyzing the mass by the above-described method are shown in FIG. 3.

From a decrease in molecular weight corresponding to dehydration of one molecule, introduction of an azoline derivative structure was verified.

3. Heating Under Basic Condition

Next, the reaction liquid was adjusted to be basic by adding 500 mM CAPS KOH (pH 11) as the below-described basic buffer. The resulting mixture was reacted at 95° C. for one hour.

Figure 4:
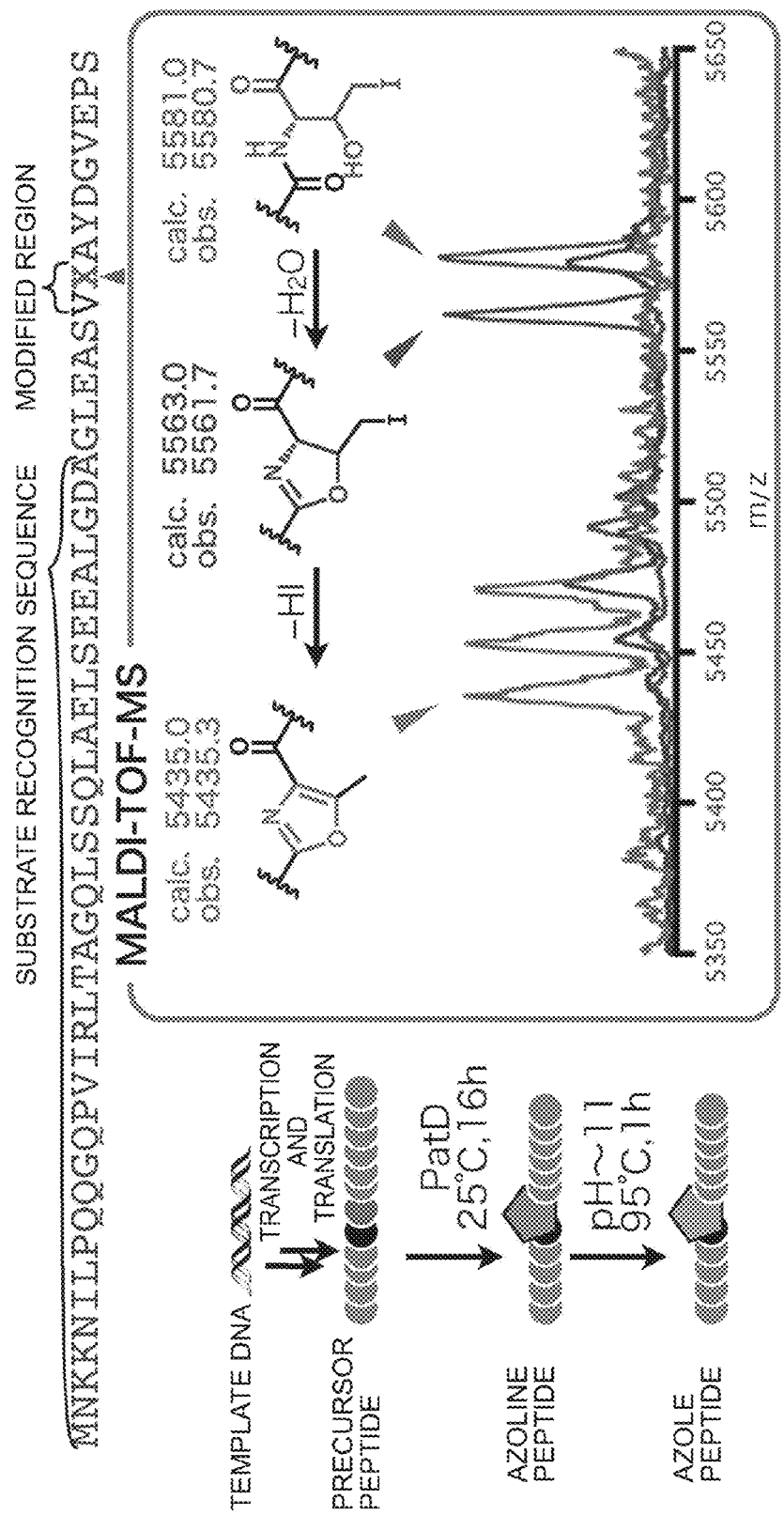
FIG. 4 shows MALDI-TOF-MS analysis results of the mass of the azoline-derivative-structure-introduced peptide after reaction at 95° C. for 1 hour at pH 11.

The results of analyzing the mass by the above-described method are shown in FIG. 4.

A decrease in molecular weight corresponding to elimination of HI was observed, which is presumed to result from the formation of an azole ring.

4. Investigation (1) of Elimination Reaction Condition

In the above 3, the following basic buffers were added and a heating reaction was performed.

500 mM CHES KOH (pH 9)
500 mM CAPS KOH (pH 11)

Figure 5:
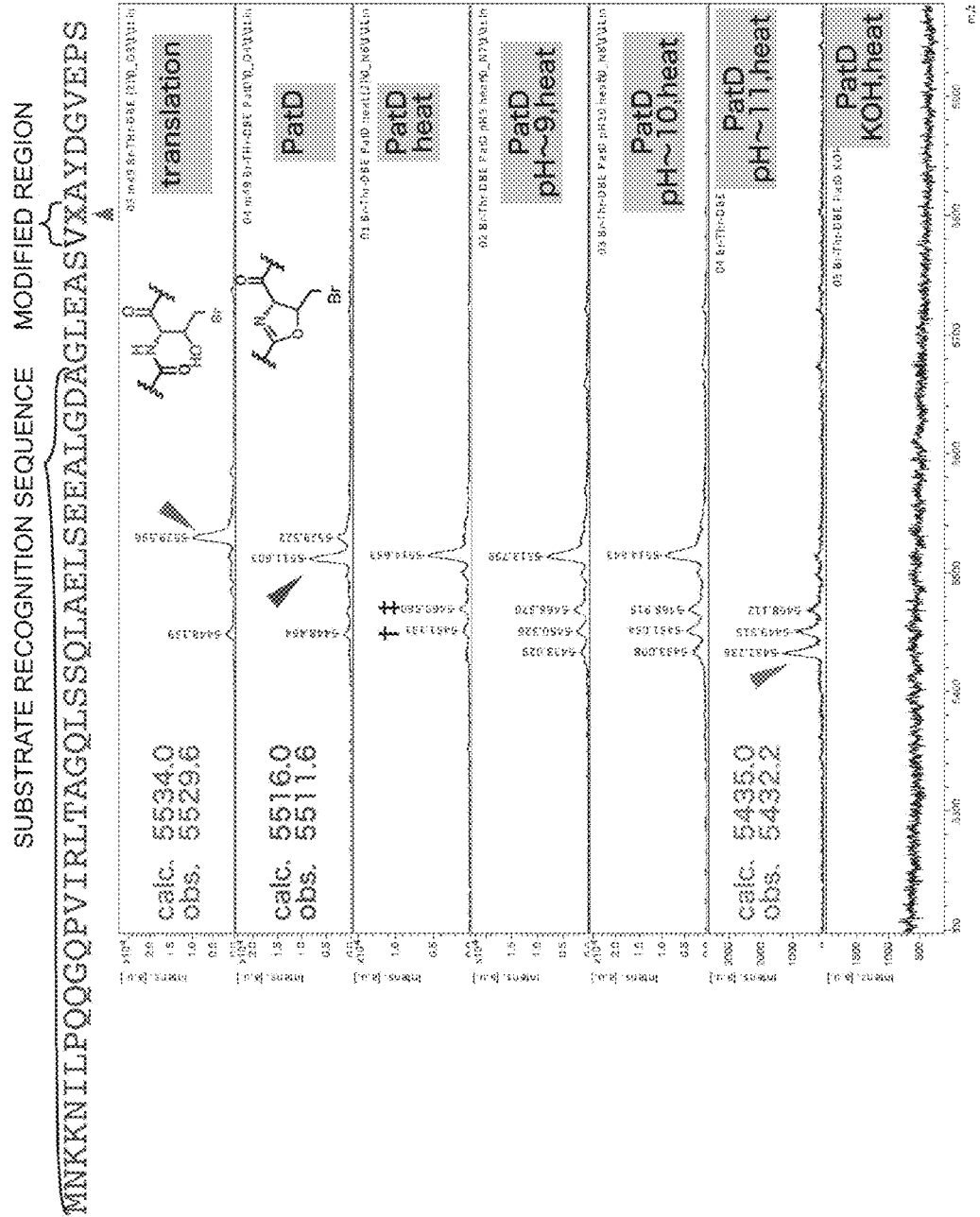
FIG. 5 shows MALDI-TOF-MS analysis results of the mass of the azoline-derivative-structure-introduced peptide after reaction at 95° C. for one hour at pH 9 or pH 11.

The results of analyzing the mass by the above-described method are shown in FIG. 5.

A decrease in molecular weight corresponding to elimination of HI was observed at pH 11, which is presumed to result from the formation of an azole ring.

5. Investigation (2) of Elimination Reaction Condition

Figure 6:
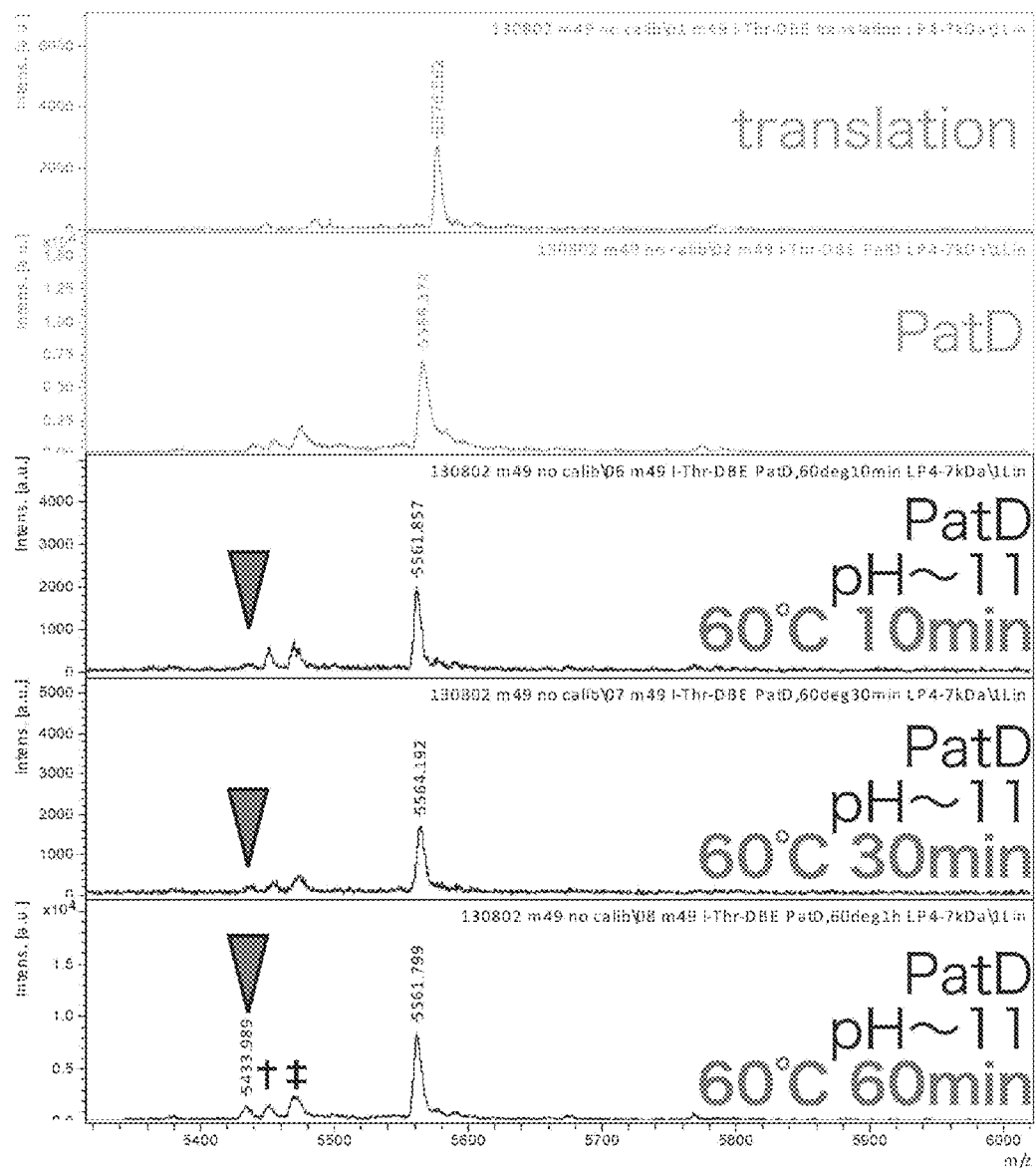
FIG. 6 shows MALDI-TOF-MS analysis results of the mass of the azoline-derivative-structure-introduced peptide after reaction at 60° C. for 10 minutes, 30 minutes or one hour at pH 11.

In the above 3, the heating reaction was performed while changing the temperature to 95° C., 60° C., or 42° C., but decrease in molecular weight corresponding to the elimination of HI was observed neither at 60° C. nor 42° C. Only the results at 60° C. are shown in FIG. 6.

6. Investigation (3) of Elimination Reaction Condition

In the above 3, 10 µL of a 10 mM, 100 µM, or 1 µM solution of diazabicycloundecene (DBU) was added instead of 500 mM CAPS KOH (pH 11). The resulting mixture was reacted at 95° C. for 30 minutes.

Figure 7:
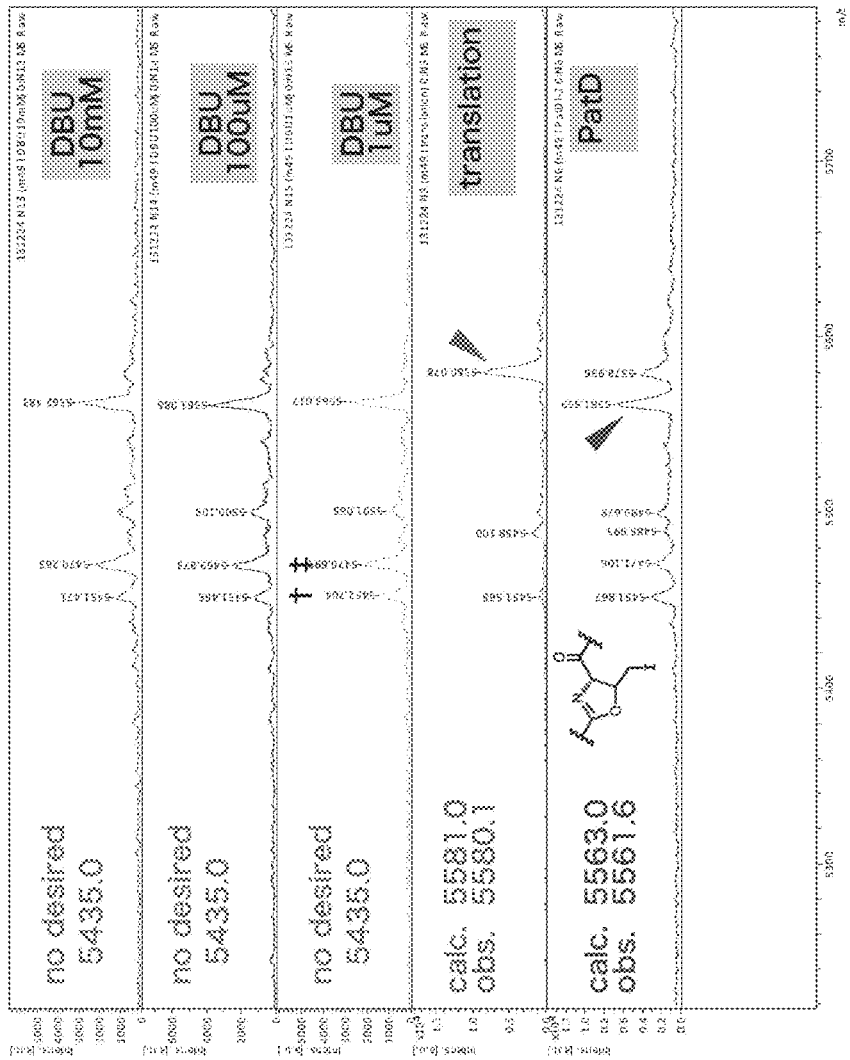
FIG. 7 shows MALDI-TOF-MS analysis results of the mass of the azoline-derivative-structure-introduced peptide after reaction at 95° C. for 30 minutes in the presence of DBU (10 mM, 100 μM, or 1 μM).

The results are shown in FIG. 7. Introduction of an azoline derivative structure was verified but it was not converted into an azole derivative structure. A similar test was made using, as X, an amino acid having Br or Cl as $X_2$, but not azole ring was formed (no data shown).

7. Investigation (4) of Elimination Reaction Condition

In the above 3, 10 µL of 10 mM Ag+ was added instead of 500 mM CAPS KOH (pH 11) and the reaction was made at pH adjusted to 7.5, 9 or 10 and at a temperature of 95° C. or 37° C. for 30 minutes. The results at 95° C. are shown in FIG. 8. Formation of an azole ring was not recognized. Similarly, an azole ring was not formed at 37° C. A similar test was made using, as X, an amino acid having Br or Cl as $X_2$, but no azole ring was formed (no data shown).

Referential Example: PatG Enzyme Reaction

Instead of the above reaction in 3, an enzyme reaction with a PatG variant was performed. During the PatD reaction, PatG was added and the final concentrations of PatD and Pat G were adjusted to 1 μM and from 2.9 μM to 5.3 μM, respectively, followed by reaction at 25° C. for 16 hours. Then, trifluoroacetic acid was added to give a final concentration of 1% and the resulting mixture was reacted at 95° C. for 5 minutes.

Figure 9:
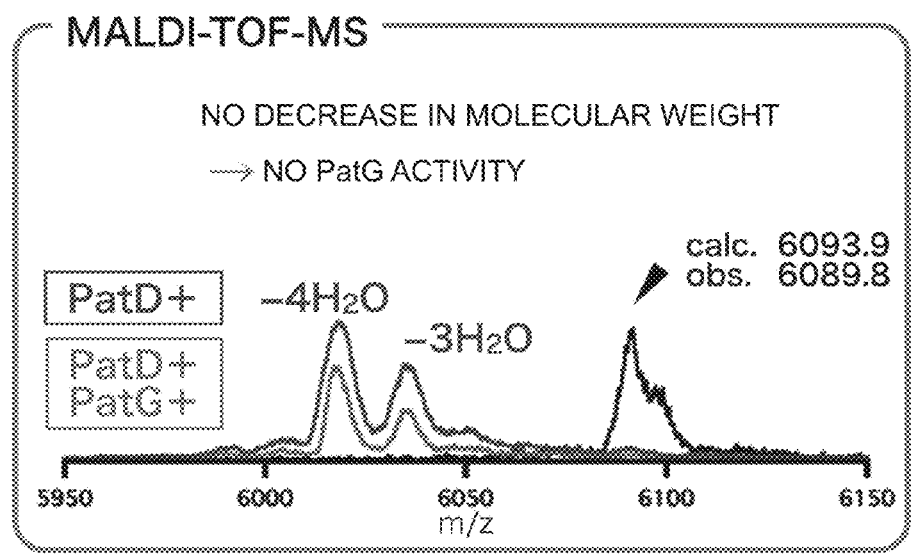
FIG. 9 shows MALDI-TOF-MS analysis results of the mass of the azoline-derivative-structure-introduced peptide after reaction with PatG.
Figure 10:
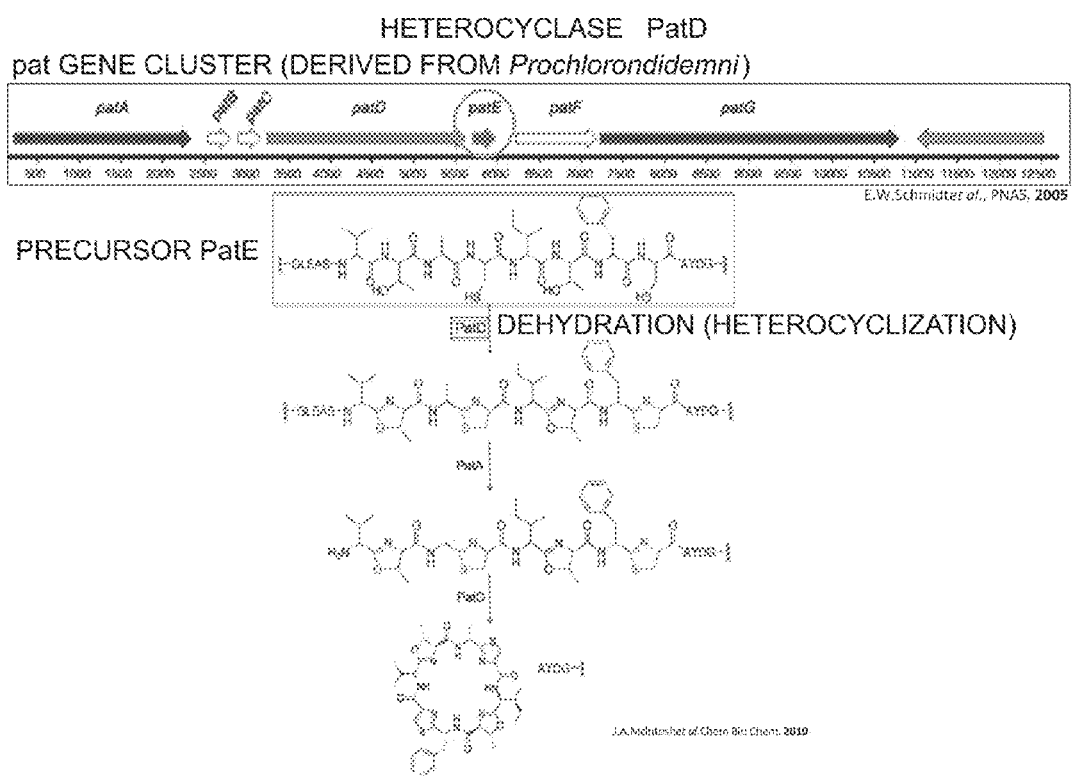
FIG. 10 schematically shows a pat gene cluster and a biosynthesis pathway thereof.

The results of analyzing the mass by the above-described method are shown in FIG. 9. Neither decrease in molecular weight due to the reaction with PatG nor peak showing resistance against hydrolysis conditions with trifluoroacetic acid was observed (no data shown). Thus, formation of an azole ring was not recognized.

Sequence Listing Free Text

SEQ ID NOS: 1 to 4 are amino acid sequences of a leader sequence in the substrate peptide of an azoline structure introducing enzyme.

SEQ ID NOS: 5 and 6 are amino acid sequences of the recognition sequence 1 in the substrate peptide of an azoline structure introducing enzyme.

SEQ ID NOS: 7 to 16 are amino acid sequences of the recognition sequence 2 in the substrate peptide of an azoline structure introducing enzyme.

SEQ ID NO: 17 is an amino acid sequence of the substrate peptide used in Example.

SEQ ID NOS: 18 and 19 are amino acid sequences of a sense chain and an anti-sense chain used in the translation of the substrate peptide, respectively.

What is claimed is:

1. A method of producing a peptide having, in the backbone thereof, an azole derivative structure, comprising the steps of:

synthesizing a substrate peptide of an azoline structure introducing enzyme having, in a modified region thereof, at least one of the following amino acids;

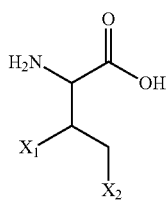

Chemical formula 1

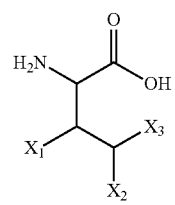

Chemical formula 2

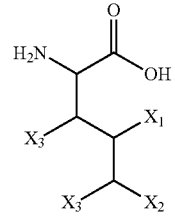

Chemical formula 3

-continued

Chemical formula 4

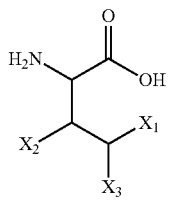

wherein
- X₁ represents a group selected from the group consisting of SH, OH, NH₂, SR¹, OR¹, NHR¹, and N₃, wherein R¹ represents a protecting group),
- X₂ represents an easily eliminable group; and
- X₃ represents hydrogen or a substituted or unsubstituted alkyl or aryl group having from 1 to 10 carbon atoms;

reacting the substrate peptide with an azoline structure introducing enzyme to obtain a peptide having an azoline derivative structure; and converting the azoline derivative structure of the resulting peptide into an azole derivative structure by inducing HX₂ elimination reaction of X₂ group.

2. The method according to claim 1, wherein X₂ is a group selected from the group consisting of Cl, Br, I, OTs, OMs, and N⁺R²₃, wherein R² is independently selected from hydrogen or a substituted or unsubstituted alkyl or aryl group having from 1 to 10 carbon atoms.

3. The method according to claim 1, wherein the amino acid is represented by the following formula:

Chemical formula 5

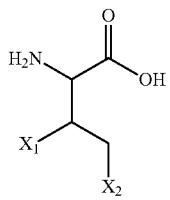

wherein, X₁ represents OH and X₂ represents Cl, Br, or I.

4. The method according to claim 1, wherein the elimination reaction is performed at pH>9.

5. The method according to claim 1, wherein the elimination reaction is performed at 80° C. or more.

6. The method according to claim 1, further comprising a step of macrocyclizing the peptide.

7. The method according to claim 1, wherein the substrate peptide does not contain a leader sequence.

8. The method according to claim 1, wherein the substrate peptide further contains, in the modified region thereof or in a region other than the modified region, at least one non-protein amino acid.

9. A method of constructing a peptide library having, in the backbone thereof, an azole derivative structure, comprising the steps of:
- constructing an mRNA library encoding a substrate peptide library including two or more substrate peptides of an azoline structure introducing enzyme different in sequence of a modified region, the substrate peptides each containing, in the modified region thereof, at least any one of the following amino acids:

Chemical formula 6

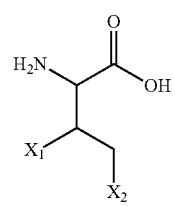

Chemical formula 7

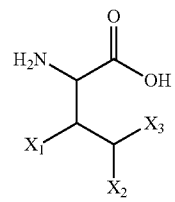

Chemical formula 8

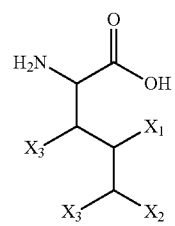

Chemical formula 9

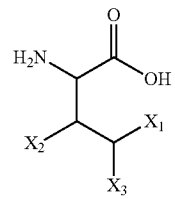

wherein
- X₁ represents a group selected from the group consisting of SH, OH, NH₂, SR¹, OR¹, NHR¹, and N₃, wherein R¹ represents a protecting group,
- X₂ represents an easily eliminable group; and
- X₃ represents hydrogen or a substituted or unsubstituted alkyl or aryl group having from 1 to 10 carbon atoms;

translating the mRNA library in a cell-free translation system to obtain a substrate peptide library;

reacting the substrate peptide library with an azoline structure introducing enzyme to obtain a peptide library having an azoline derivative structure; and obtaining a peptide library having an azole derivative structure by inducing an elimination reaction of X₂ group and thereby converting the azoline derivative structure of the peptide library having an azoline derivative structure into an azole derivative structure.

10. The method according to claim 9, wherein X₂ is a group selected from the group consisting of Cl, Br, I, OTs, OMs, and N⁺R²₃, wherein R² is independently selected from hydrogen or a substituted or unsubstituted alkyl or aryl group having from 1 to 10 carbon atoms.

11. The method according to claim 9, wherein the amino acid is represented by the following formula:

Chemical formula 10

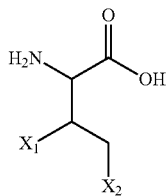

wherein, $X_1$ represents OH and $X_2$ represents Cl, Br, or I.

12. The method according to claim 9, wherein the elimination reaction is performed at pH>9.

13. The method according to claim 9, wherein the heating reaction is performed at 80° C. or more.

14. The method according to claim 9, further comprising a step of macrocyclizing the peptide.

15. The method according to claim 9, wherein the substrate peptide does not contain a leader sequence and the azoline structure introducing enzyme has a leader sequence bound thereto.

16. The method according to claim 9, wherein the substrate peptide further contains, in the modified region thereof or in a region other than the modified region, at least one non-protein amino acid.

17. The method according to claim 9, wherein the step of constructing an mRNA library includes a step of binding puromycin to the 3' end of each mRNA of the mRNA library, and an mRNA-bound substrate peptide library is obtained in the step of obtaining a substrate peptide library.

18. A screening method for identifying a peptide having an azole derivative structure that binds to a target substance, comprising the steps of:
bringing a peptide library having an azole derivative structure constructed by the method as claimed in claim 9 into contact with the target substance, followed by incubation; and
selecting a peptide having an azole derivative structure that has bound to the target substance.

19. A screening method for identifying a peptide having an azole derivative structure that binds to a target substance, comprising the steps of:
bringing an mRNA-bound peptide library having an azole derivative structure constructed by the method as claimed in claim 17 into contact with the target substance, followed by incubation;
collecting an mRNA-bound peptide cluster having an azole derivative structure that has bound to the target substance;
obtaining, from an mRNA portion of the collected mRNA-bound peptide cluster, a cDNA cluster by a reverse transcription reaction;
binding puromycin to the 3' end of the cDNA cluster, followed by translation to obtain an mRNA-bound peptide library; and
performing the above-described steps at least once to enrich the peptide having an azole derivative structure that binds to a target substance.

20. A screening method for identifying a peptide having an azole derivative structure that binds to a target substance, comprising the steps of:
obtaining, from an mRNA-bound peptide library having an azole derivative structure constructed by the method as claimed in claim 17, a DNA-bound peptide library having an azole derivative structure by a reverse transcription reaction;
bringing the DNA-bound peptide library having an azole derivative structure into contact with the target substance, followed by incubation;
collecting a DNA-bound peptide cluster having an azole derivative structure that has bound to the target substance and amplifying a DNA portion of the cluster;
binding puromycin to the 3' end of the amplified DNA cluster, followed by translation to obtain an mRNA-bound peptide library; and
performing the above-described steps at least once to enrich a peptide having an azole derivative structure that binds to the target substance.

* * * * *

```
                        SEQUENCE LISTING

<160> NUMBER OF SEQ ID NOS: 19

<210> SEQ ID NO 1
<211> LENGTH: 37
<212> TYPE: PRT
<213> ORGANISM: Prochloron didemni
<220> FEATURE:
<221> NAME/KEY: MISC_FEATURE
<223> OTHER INFORMATION: The leader sequence of PatE.

<400> SEQUENCE: 1

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30

Ala Leu Gly Asp Ala
        35

<210> SEQ ID NO 2
<211> LENGTH: 24
<212> TYPE: PRT
<213> ORGANISM: Streptococcus lactis
<220> FEATURE:
<221> NAME/KEY: MISC_FEATURE
<223> OTHER INFORMATION: A leader sequence in a substrate peptide for
      azoline-backbone-int roducing enzymes.

<400> SEQUENCE: 2

Met Lys Glu Gln Asn Ser Phe Asn Leu Leu Gln Glu Val Thr Glu Ser
1               5                   10                  15

Glu Leu Asp Leu Ile Leu Gly Ala
            20

<210> SEQ ID NO 3
<211> LENGTH: 25
<212> TYPE: PRT
<213> ORGANISM: Homo sapiens
<220> FEATURE:
<221> NAME/KEY: MISC_FEATURE
<223> OTHER INFORMATION: A leader sequence in a substrate peptide for
      azoline-backbone-int roducing enzymes.

<400> SEQUENCE: 3

Met Ile Leu Ala Ser Leu Ser Thr Phe Gln Gln Met Trp Ile Ser Lys
1               5                   10                  15

Gln Glu Tyr Asp Glu Ala Gly Asp Ala
            20                  25
```

```
<210> SEQ ID NO 4
<211> LENGTH: 37
<212> TYPE: PRT
<213> ORGANISM: Artificial
<220> FEATURE:
<223> OTHER INFORMATION: A synthesized peptide.  A leader sequence in
      a substrate peptide for azoline-backbone-introducing enzymes.

<400> SEQUENCE: 4

Met Glu Leu Gln Leu Arg Pro Ser Gly Leu Glu Lys Lys Gln Ala Pro
1               5                  10                  15

Ile Ser Glu Leu Asn Ile Ala Gln Thr Gln Gly Gly Asp Ser Gln Val
            20                  25                  30

Leu Ala Leu Asn Ala
        35

<210> SEQ ID NO 5
<211> LENGTH: 5
<212> TYPE: PRT
<213> ORGANISM: Artificial
<220> FEATURE:
<223> OTHER INFORMATION: A synthesized peptide.  Recognition sequence 1
      in a substrate peptide for azoline-backbone-introducing enzymes.
<220> FEATURE:
<221> NAME/KEY: MISC_FEATURE
<222> LOCATION: (2)..(2)
<223> OTHER INFORMATION: Xaa is Ala, Leu or Val.
<220> FEATURE:
<221> NAME/KEY: MISC_FEATURE
<222> LOCATION: (3)..(3)
<223> OTHER INFORMATION: Xaa is Gly, Glu or Asp.
<220> FEATURE:
<221> NAME/KEY: MISC_FEATURE
<222> LOCATION: (4)..(4)
<223> OTHER INFORMATION: Xaa is Ala or Pro.
<220> FEATURE:
<221> NAME/KEY: MISC_FEATURE
<222> LOCATION: (5)..(5)
<223> OTHER INFORMATION: Xaa is Ser, Thr or Cys.

<400> SEQUENCE: 5

Gly Xaa Xaa Xaa Xaa
1               5

<210> SEQ ID NO 6
<211> LENGTH: 5
<212> TYPE: PRT
<213> ORGANISM: Artificial
<220> FEATURE:
<223> OTHER INFORMATION: A synthesized peptide.  Recognition sequence 1
      in a substrate peptide for azoline-backbone-introducing enzymes.

<400> SEQUENCE: 6

Gly Leu Glu Ala Ser
1               5

<210> SEQ ID NO 7
<211> LENGTH: 5
<212> TYPE: PRT
<213> ORGANISM: Artificial
<220> FEATURE:
<223> OTHER INFORMATION: A synthesized peptide.  Recognition sequence 2
      in a substrate peptide for azoline-backbone-introducing enzymes.
<220> FEATURE:
<221> NAME/KEY: MISC_FEATURE
<222> LOCATION: (1)..(1)
<223> OTHER INFORMATION: Xaa is Ala or Ser.
<220> FEATURE:
<221> NAME/KEY: MISC_FEATURE
```

```
<222> LOCATION: (3)..(3)
<223> OTHER INFORMATION: Xaa is Asp or Glu.
<220> FEATURE:
<221> NAME/KEY: MISC_FEATURE
<222> LOCATION: (5)..(5)
<223> OTHER INFORMATION: Xaa is Ala, Leu or Val.

<400> SEQUENCE: 7

Xaa Tyr Xaa Gly Xaa
1               5

<210> SEQ ID NO 8
<211> LENGTH: 8
<212> TYPE: PRT
<213> ORGANISM: Artificial
<220> FEATURE:
<223> OTHER INFORMATION: A synthesized peptide.  Recognition sequence 2
      in a substrate peptide for azoline-backbone-introducing enzymes.

<400> SEQUENCE: 8

Ala Tyr Asp Gly Val Glu Pro Ser
1               5

<210> SEQ ID NO 9
<211> LENGTH: 5
<212> TYPE: PRT
<213> ORGANISM: Artificial
<220> FEATURE:
<223> OTHER INFORMATION: A synthesized peptide.  Recognition sequence 2
      in a substrate peptide for azoline-backbone-introducing enzymes.

<400> SEQUENCE: 9

Ala Tyr Asp Gly Val
1               5

<210> SEQ ID NO 10
<211> LENGTH: 11
<212> TYPE: PRT
<213> ORGANISM: Artificial
<220> FEATURE:
<223> OTHER INFORMATION: A synthesized peptide.  Recognition sequence 2
      in a substrate peptide for azoline-backbone-introducing enzymes.

<400> SEQUENCE: 10

Ala Tyr Asp Gly Val Gly Ser Gly Ser Gly Ser
1               5                   10

<210> SEQ ID NO 11
<211> LENGTH: 11
<212> TYPE: PRT
<213> ORGANISM: Artificial
<220> FEATURE:
<223> OTHER INFORMATION: A synthesized peptide.  Recognition sequence 2
      in a substrate peptide for azoline-backbone-introducing enzymes.

<400> SEQUENCE: 11

Ala Tyr Asp Gly Val Gly Gly Gly Gly Gly Gly
1               5                   10

<210> SEQ ID NO 12
<211> LENGTH: 12
<212> TYPE: PRT
<213> ORGANISM: Artificial
<220> FEATURE:
<223> OTHER INFORMATION: A synthesized peptide.  Recognition sequence 2
      in a substrate peptide for azoline-backbone-introducing enzymes.

<400> SEQUENCE: 12
```

```
Ala Tyr Asp Gly Val Glu Gly Ser Gly Ser Gly Ser
1               5                   10
```

```
<210> SEQ ID NO 13
<211> LENGTH: 5
<212> TYPE: PRT
<213> ORGANISM: Artificial
<220> FEATURE:
<223> OTHER INFORMATION: A synthesized peptide.  Recognition sequence 2
      in a substrate peptide for azoline-backbone-introducing enzymes.

<400> SEQUENCE: 13

Gly Gly Gly Gly Gly
1               5
```

```
<210> SEQ ID NO 14
<211> LENGTH: 5
<212> TYPE: PRT
<213> ORGANISM: Artificial
<220> FEATURE:
<223> OTHER INFORMATION: A synthesized peptide.  Recognition sequence 2
      in a substrate peptide for azoline-backbone-introducing enzymes.

<400> SEQUENCE: 14

Gln Gln Gln Gln Gln
1               5
```

```
<210> SEQ ID NO 15
<211> LENGTH: 5
<212> TYPE: PRT
<213> ORGANISM: Artificial
<220> FEATURE:
<223> OTHER INFORMATION: A synthesized peptide.  Recognition sequence 2
      in a substrate peptide for azoline-backbone-introducing enzymes.

<400> SEQUENCE: 15

Leu Leu Leu Leu Leu
1               5
```

```
<210> SEQ ID NO 16
<211> LENGTH: 5
<212> TYPE: PRT
<213> ORGANISM: Artificial
<220> FEATURE:
<223> OTHER INFORMATION: A synthesized peptide.  Recognition sequence 2
      in a substrate peptide for azoline-backbone-introducing enzymes.

<400> SEQUENCE: 16

Pro Pro Pro Pro Pro
1               5
```

```
<210> SEQ ID NO 17
<211> LENGTH: 52
<212> TYPE: PRT
<213> ORGANISM: Artificial
<220> FEATURE:
<223> OTHER INFORMATION: A synthesized peptide.  Amino acid sequence of
      a Substrate Peptide for azoline-backbone-introducing enzymes.
<220> FEATURE:
<221> NAME/KEY: MISC_FEATURE
<222> LOCATION: (44)..(44)
<223> OTHER INFORMATION: Xaa is a non-proteinogenic amino acid l-Thr.

<400> SEQUENCE: 17

Met Asn Lys Lys Asn Ile Leu Pro Gln Gln Gly Gln Pro Val Ile Arg
1               5                   10                  15

Leu Thr Ala Gly Gln Leu Ser Ser Gln Leu Ala Glu Leu Ser Glu Glu
            20                  25                  30
```

```
Ala Leu Gly Asp Ala Gly Leu Glu Ala Ser Val Xaa Ala Tyr Asp Gly
        35                  40                  45

Val Glu Pro Ser
    50

<210> SEQ ID NO 18
<211> LENGTH: 212
<212> TYPE: DNA
<213> ORGANISM: Artificial
<220> FEATURE:
<223> OTHER INFORMATION: Sense sequence coding a Substrate Peptide for
      azoline-backbone-in troducing enzymes.
<220> FEATURE:
<221> NAME/KEY: misc_feature
<222> LOCATION: (48)..(203)
<223> OTHER INFORMATION: Coding region of a Substrate Peptide.
<220> FEATURE:
<221> NAME/KEY: misc_feature
<222> LOCATION: (177)..(179)
<223> OTHER INFORMATION: "TGT" codes for a non-proteinogenic amino acid
      I-Thr.

<400> SEQUENCE: 18
ggcgtaatac gactcactat agggttaact ttaacaagga gaaaaacatg aacaagaaaa      60
acatcctgcc ccaacaaggt caaccggtta tccgcttaac cgcaggacag ttgagctcgc     120
aactcgccga actgtctgaa gaagcactgg gcgacgcggg gttggaggca agcgtttgtg     180
cgtacgatgg cgttgagcca tcttaagctt cg                                   212

<210> SEQ ID NO 19
<211> LENGTH: 212
<212> TYPE: DNA
<213> ORGANISM: Artificial
<220> FEATURE:
<223> OTHER INFORMATION: Antisense sequence coding a Substrate Peptide
      for azoline-backbone-introducing enzymes.

<400> SEQUENCE: 19
cgaagcttaa gatggctcaa cgccatcgta cgcacaaacg cttgcctcca accccgcgtc      60
gcccagtgct tcttcagaca gttcggcgag ttgcgagctc aactgtcctg cggttaagcg     120
gataaccggt tgaccttgtt ggggcaggat gttttcttg ttcatgtttt tctccttgtt     180
aaagttaacc ctatagtgag tcgtattacg cc                                   212
```